(12) United States Patent
Questo et al.

(10) Patent No.: US 8,776,625 B2
(45) Date of Patent: Jul. 15, 2014

(54) SONIC RESONATOR SYSTEM FOR USE IN BIOMEDICAL APPLICATIONS

(75) Inventors: Warren Questo, El Dorado Hills, CA (US); Claudio Zanelli, Menlo Park, CA (US); Carl W. Hennige, Folsom, CA (US); Jason R. Wetsel, Cameron Park, CA (US)

(73) Assignee: Focus-In-Time, LLC, Cameron Park, CA (US)

( * ) Notice: Subject to any disclaimer, the term of this patent is extended or adjusted under 35 U.S.C. 154(b) by 777 days.

(21) Appl. No.: 12/800,735

(22) Filed: May 21, 2010

(65) Prior Publication Data
US 2011/0288457 A1    Nov. 24, 2011

(51) Int. Cl.
*G01N 29/07* (2006.01)
*G01N 29/09* (2006.01)
*G01N 29/265* (2006.01)
*G01N 29/30* (2006.01)

(52) U.S. Cl.
USPC ............. 73/866.5; 73/584; 73/618; 73/630

(58) Field of Classification Search
USPC .......... 73/584, 588, 763, 774, 781, 818, 821, 73/865.8, 866.5, 1.82, 618, 630
See application file for complete search history.

(56) References Cited

U.S. PATENT DOCUMENTS

| | | | |
|---|---|---|---|
| 2,846,874 A * | 8/1958 | Horn | 73/588 |
| 3,924,444 A * | 12/1975 | Heyman et al. | 73/1.85 |
| 4,397,186 A * | 8/1983 | Phelan et al. | 73/584 |
| 4,447,301 A * | 5/1984 | Shen | 205/336 |
| 4,622,969 A * | 11/1986 | Forssmann et al. | 601/4 |
| 4,674,505 A * | 6/1987 | Pauli et al. | 601/4 |
| 4,721,106 A * | 1/1988 | Kurtze et al. | 601/4 |
| 4,972,826 A * | 11/1990 | Koehler et al. | 601/4 |
| 5,143,063 A | 9/1992 | Fellner | 128/399 |
| 5,172,344 A * | 12/1992 | Ehrlich | 367/152 |
| 5,309,897 A * | 5/1994 | Hassler et al. | 601/4 |
| 5,438,554 A * | 8/1995 | Seyed-Bolorforosh et al. | 367/140 |
| 5,465,722 A * | 11/1995 | Fort et al. | 600/447 |
| 5,827,204 A | 10/1998 | Grandin et al. | 301/2 |
| 6,071,239 A | 6/2000 | Cribbs et al. | 600/439 |
| 6,383,152 B1 * | 5/2002 | Hartmann et al. | 601/4 |
| 6,443,900 B2 * | 9/2002 | Adachi et al. | 600/458 |
| 6,607,498 B2 * | 8/2003 | Eshel | 601/2 |
| 6,617,760 B1 * | 9/2003 | Peterson et al. | 310/328 |
| 6,716,184 B2 | 4/2004 | Vaezy | 601/3 |
| 7,258,674 B2 | 8/2007 | Cribbs et al. | 601/2 |
| 7,347,855 B2 | 3/2008 | Eshel et al. | 606/2.5 |
| 7,510,536 B2 | 3/2009 | Foley et al. | 601/2 |
| 8,074,520 B2 * | 12/2011 | Hirose et al. | 73/622 |
| 8,109,878 B1 * | 2/2012 | O'Ruanaidh et al. | 600/443 |
| 2006/0244340 A1 * | 11/2006 | Marathe et al. | 310/321 |
| 2007/0080609 A1 * | 4/2007 | Johnson et al. | 310/323.04 |
| 2009/0079300 A1 * | 3/2009 | Hielscher et al. | 310/324 |

* cited by examiner

*Primary Examiner* — David A Rogers
(74) *Attorney, Agent, or Firm* — Shirley L. Church, Esq.

(57) ABSTRACT

Disclosed herein is a sonic resonator system and a method of using the system which is useful in therapeutic, cosmetic or aesthetic, diagnostic, exploratory and other medical procedures, particularly where a relatively non-invasive procedure is needed. The sonic resonator system and its method of use provide a controllable high intensity sonic impulse, which may be in the form of a compression or rarefaction wave applied to a given target tissue or anatomical structure, to cause a significant therapeutic or other physiological effect.

15 Claims, 14 Drawing Sheets

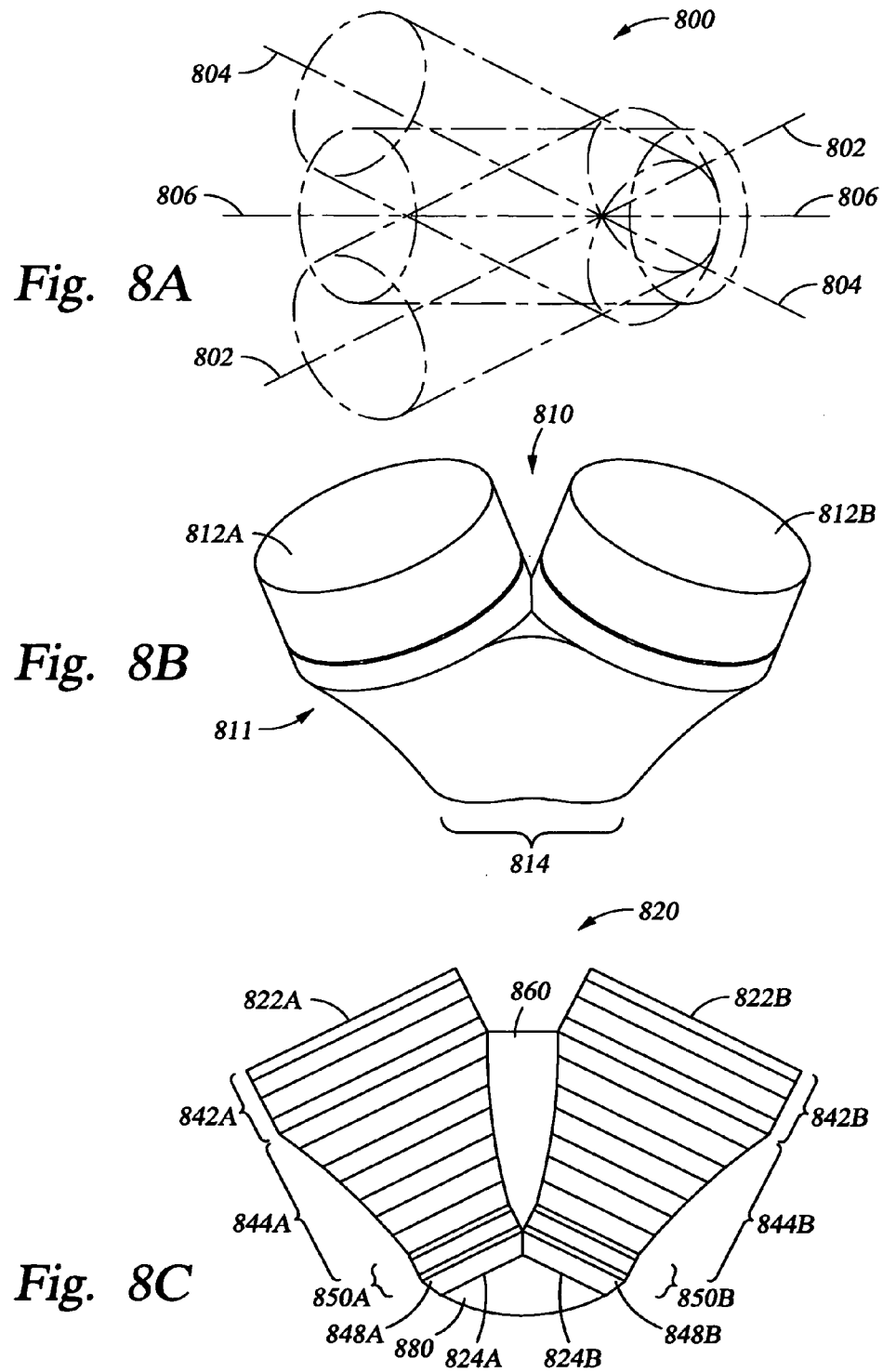

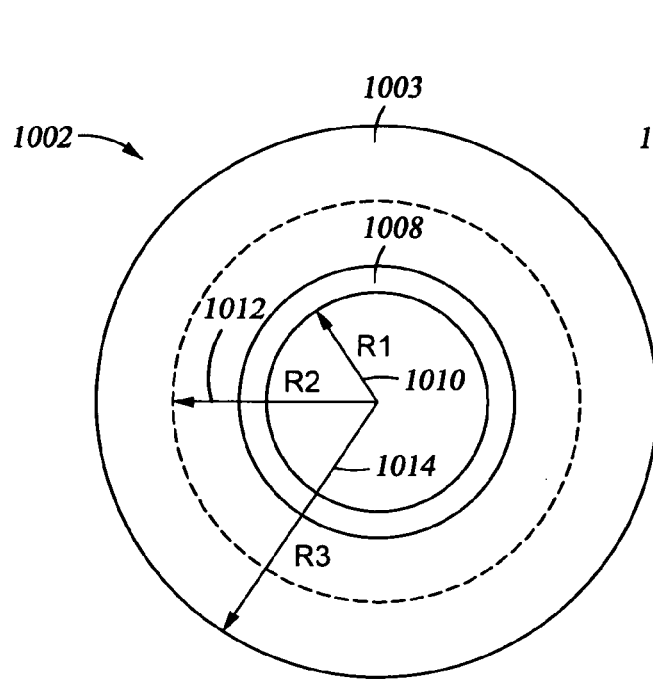
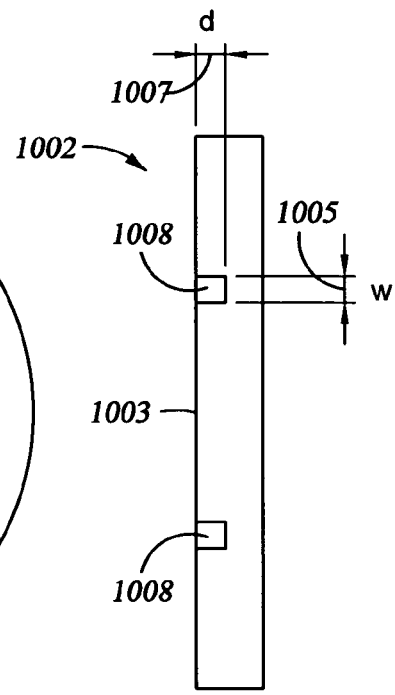
*Fig. 10A*  *Fig. 10B*
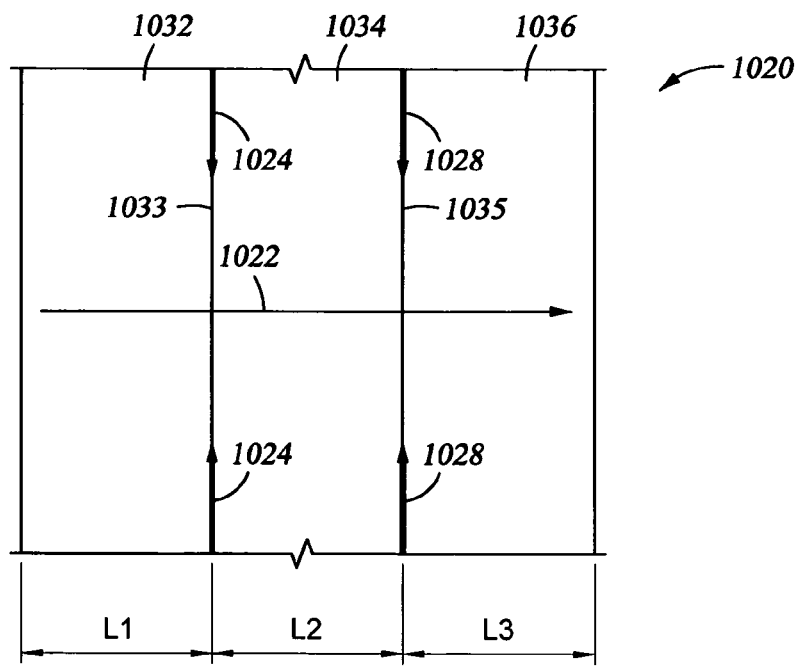
*Fig. 10C*

SONIC RESONATOR SYSTEM FOR USE IN BIOMEDICAL APPLICATIONS

BACKGROUND

1. Field

The invention pertains to a sonic resonator system for use in biomedical applications. The invention also pertains to a method of calibrating the sonic resonator system and to methods of using the sonic resonator system in various biomedical applications.

2. Description of the Background Art

This section describes background subject matter related to the disclosed embodiments of the present invention. There is no intention, either express or implied, that the background art discussed in this section legally constitutes prior art.

There are numerous non-invasive biomedical procedures which can benefit from the use of high intensity, wide bandwidth ultrasonic impulses. Conventional technology is capable of delivering high sonic intensities as a sonic shock wave or as a continuous sonic wave (CW), where conventional devices deliver high intensities of sonic energy focused to a point in space. There exist several methods of achieving this spatial focus, including the shaping of piezoelectric elements.

One example of such a piezoelectric element is a high-intensity focused ultrasound (HIFU) transducer, which is shaped to form a spherical lens to focus the sonic energy. FIG. 1 shows this concept, where the diagram 100 shows a transducer 102 shaped to form a spherical lens 104, to produce focused energy at a point in space 106. In another embodiment (not shown), a plurality of sonic elements having a desired shape can be arranged in a mosaic in order to achieve mechanical focus. An array of elements could have any shape (e.g., flat); the elements are then "fired" with the appropriate delay in order to create a focus and/or steer the beam. This is known as a "phased array".

In an even older example, lithotripters utilize a concave mirror to focus the energy from a "spark plug" sonic source. In all of these earlier examples, focus is achieved by an array of elements and/or the physical construct of the sonic device; for example, by forming the piezoelectric element to have a particular shape, using a lens assembly or by electronic delay of the excitation pulses (e.g., a phase array) to focus the sonic energy to a specific point in space.

When piezoelectric elements are used to achieve spatial focus, high intensity sonic impulses are typically achieved by applying a high voltage impulse across the piezoelectric element. There are limits to the voltage that can be applied and, hence, to the resulting sonic amplitude. If the voltage is too high, it can "de-pole" the ceramic of the piezoelectric element, arc across the piezoelectric element, or produce a strain so high that it fractures the piezoelectric element. These and other effects limit the maximum amplitude sonic pulse that can be generated using conventional methods.

Another practical limitation of the current technology is that higher sonic intensities are generated using narrow bandwidth transducers operating over a narrow frequency range in a resonant continuous wave (CW) mode. However, wide bandwidth impulses of high sonic intensity cannot be generated using narrow bandwidth devices. In medical applications, there are several advantages in having the ability to generate an impulse having a wide bandwidth. Conventional continuous wave (CW), fixed-focus sonic devices cannot deliver a high intensity impulse that can create very high sonic pressures with short duration particle velocities.

In general, broadband sonic performance has been achieved at the expense of efficiency. This broadband performance might be achieved by absorbing a portion of the generated sonic energy in the transducer to damp the resonance. Or, the broadband performance might be accomplished by operating the transducer far from its natural resonance, where its ability to generate large amplitude sonic signals is poor.

The following are descriptions of various biomedical methods and apparatus known in the art:

U.S. Pat. No. 5,143,063, to Fellner, discloses electromedical apparatus which is employed to non-invasively remove adipose tissue from the body by causing necrosis of the tissue, by localizing (e.g., focusing) radiant energy. The radiant energy may be of any suitable kind, for example, localized radiofrequency, microwave, or ultrasound energy, which is impinged upon the cells to be eliminated. Cell destruction occurs through a mechanism such as heating or mechanical disruption beyond a level which the adipose tissue can survive. (Abstract)

U.S. Pat. No. 5,827,204, to Grandia et al., discloses medical noninvasive operations using focused modulated high power ultrasound, which generally includes a transmitter for exciting a multifrequency ultrasound wave for causing vaporous cavitation bubbles in a small focal zone of a medical target region. A low frequency signal is induced at a level slightly below that required for causing cavitation and a high frequency signal is superimposed on the low frequency signal to exceed the cavitation threshold. Focused ultrasound is said to be used for both dissolving tissues, as well as causing clots in order to destroy cancerous growths. In addition, an imaging system is provided for enabling viewing of the medical target area during the therapy. (Abstract and Col. 2 lines 26-32)

U.S. Pat. No. 6,071,239, to Cribbs et al., discloses non-invasive destruction of fat cells in a living patient, without separating the skin from the body, by applying to the fat layer high intensity focused ultrasound simultaneously in a multiplicity of discrete focal zones produced by a single transducer array. A phasing apparatus for producing a widely variable set of focal zone patterns for lipolytic therapy and other purposes is disclosed. (Abstract)

U.S. Pat. No. 6,607,498, to Eshel, discloses a method and apparatus for producing lysis of adipose tissue underlying the skin of a subject by applying an ultrasonic transducer to the subject's skin to transmit therethrough ultrasonic waves focused on the adipose tissue, and electrically actuating the ultrasonic transducer to transmit ultrasonic waves to produce cavitational lysis of the adipose tissue without damaging non-adipose tissue. (Abstract)

U.S. Pat. No. 6,716,184, to Vaezy et al., discloses a method and apparatus for the simultaneous use of ultrasound on a probe for imaging and therapeutic purposes. The probe limits the effects of undesirable interference noise in a display by synchronizing HIFU waves with an imaging transducer to cause the noise to be displayed in an area of the image that does not overlap the treatment site. In one embodiment, the HIFU is first energized at a low power level that does not cause tissue damage, so that the focal point of the HIFU can be identified by a change in the echogenicity of the tissue caused by the HIFU. Once the focal point is properly targeted on a desired treatment site, the power level is increased to a therapeutic level. The location of each treatment site is stored and displayed to the user to enable a plurality of spaced-apart treatment sites to be achieved. A preferred application of the HIFU waves is to cause lesions in blood vessels, so that the supply of nutrients and oxygen to a region, such as a tumor, is interrupted. The tumor will thus eventually be destroyed. (Abstract)

U.S. Pat. No. 7,258,674, to Cribbs et al., discloses a system for the destruction of adipose tissue utilizing HIFU within a patient's body. The system comprises a controller for data storage and the operation and control of a plurality of elements. One element is a means for mapping a human body to establish three-dimensional coordinate position data for existing adipose tissue. The controller is able to identify the plurality of adipose tissue locations on the human body and establish a protocol for the destruction of the adipose tissue. A HIFU transducer assembly having one or more piezoelectric element(s) is used along with at least one sensor, wherein the sensor provides feedback information to the controller for the safe operation of the piezoelectric element(s). The sensor is electronically coupled to the controller, and the controller provides essential treatment command information to one or more piezoelectric element(s) based on positioning information obtained from the three-dimensional coordinate position data. (Abstract)

U.S. Pat. No. 7,347,855, to Eshel et al., discloses a methodology and system for lysing adipose tissue including directing ultrasonic energy at a multiplicity of target volumes within the region, which target volumes contain adipose tissue, in order to selectively lyse the adipose tissue in the target volumes and generally not lyse non-adipose tissue in the target volumes, and computerized tracking of the multiplicity of target volumes notwithstanding movement of the body. (Abstract)

U.S. Pat. No. 7,510,536, to Foley et al., discloses a method for using HIFU to treat neurological structures to achieve a desired therapeutic effect. Depending on the dosage of HIFU applied, it can have a reversible or irreversible effect on neural structures. For example, a relatively high dose of HIFU can be used to permanently block nerve function, to provide a non-invasive alternative to severing a nerve to treat severe spasticity. Relatively lower doses of HIFU can be used to reversibly block nerve function, to alleviate pain, to achieve an anaesthetic effect, or to achieve a cosmetic effect. Where sensory nerves are not necessary for voluntary function, but are involved in pain associate with tumors or bone cancer, HIFU can be used to non-invasively destroy such sensory nerves to alleviate pain without drugs. (Abstract)

The disclosures of the above-cited references are hereby incorporated by reference herein in their entireties.

SUMMARY

Known methods of treating living tissue (such as those described above) can be time-consuming, costly, and, ultimately, ineffective. Such methods can also produce heating of tissues adjacent to those being treated, leading to tissue damage and, in the worse case scenario, necrosis of otherwise healthy tissue. The present invention provides methods and apparatus for treating living tissue that result in a maximum amount of sonic power being applied to the tissue for a minimum amount of time, thereby reducing or entirely avoiding "collateral damage" to tissues adjacent the tissue being treated. A sharp burst (impulse) of sonic power is typically applied to the tissue for such a brief amount of time that heating of tissue in the area surrounding the burst is essentially negligible.

Disclosed herein are an apparatus including a sonic resonator system, and methods of using the apparatus in therapeutic, cosmetic or aesthetic, diagnostic, exploratory and other medical procedures, particularly where the procedures are relatively non-invasive. The apparatus and methods provide a controllable high intensity sonic impulse which is applied in the form of a power pulse to a given target tissue or anatomical structure, to cause a significant therapeutic or other physiological effect. Applications for this invention may include, but are not limited to, lysing adipose tissue, hair removal, cancer treatment, kidney stone fragmentation, treatment of vascular lesions, tattoo removal, collagen shrinkage, dental treatments, treatment of spider veins, and bone repair, by way of example and not by way of limitation.

An embodiment of the apparatus including a sonic resonator system comprises a waveform generation device which supplies an electrical signal for driving a transducer, a transducer that converts electrical energy into acoustic energy, a resonator that stores this energy, and a coupling device which enables transfer of the sonic energy to a biomaterial to be treated. The waveform generator is capable of driving the transducer to produce a wideband acoustic impulse having a significantly higher (by way of example, greater than 1,000 times higher) peak power than the peak power that can be produced by the transducer alone. The sonic resonator system can create a wide bandwidth power pulse in biomaterial at selected sonic zones within the device near field. The particular voltage waveform that produces the power pulse depends upon the resonator design and calibration procedure applied to the particular biomaterial to be affected. A method of determining the appropriate waveforms to be applied within the sonic resonator system for various applications is part of the invention embodiments which are described herein.

The sonic resonator system disclosed herein has advantageous use in biomedical applications, overcoming several disadvantages of the previously known systems. The sonic resonator system disclosed herein produces a localized high sonic intensity independent of any spatial focus apparatus. The focusing is better referred to as "focused in time" rather than "focused in space", because the focusing is achieved without spatial focus, using signal reconstruction that phase aligns the individual frequencies of sound to form a focus in time, producing a short duration high energy sonic pulse (impulse). The sonic resonator can deliver a short high amplitude sonic impulse concentrated to any specified location within its sonic near field without mechanical or spatial focus. FIG. 2 shows a schematic diagram 200 of a resonator 202 which is coupled to a biomaterial 203 in a near sonic field 204. The resonator 202 delivers concentrated sonic energy to multiple zones 206 within the near sonic field 204. The sonic resonator system overcomes one very important disadvantage of conventional fixed focal depth devices in that it does not need to have a standoff between the transducer and the surface of a bio medium/biomaterial to permit change in depth of focus. Instead, the waveform delivered to the transducer which drives the resonator is constructed by the calibration software to create the focused in time generated power pulse. Further, the sonic resonator enables delivery of a much lower average power, when desired, so that temperature rise in a bio-medium/biomaterial can be maintained within an acceptable range.

A sonic resonator assembly is specifically designed to first create a uniform, low level sonic field, and then a calibration process is applied to develop a waveform which is applied to a piezoelectric driver which feeds the resonator, to concentrate (focus) the localized sonic energy intensity at any given point in the sonic device near field. To achieve a given "focus-in-time" of an intense localized sonic energy as a power pulse within a biomedium/biomaterial at a particular location as needed, a calibration process must be used which is related to the biomaterial to be tested or treated. The calibration process depends specifically on the bio medium/biomaterial. Typically, the resulting acoustic intensity which is focused-in-time has sound pressure greater than 20 MPascal with particle velocities greater than 30 meters/second. The high acoustic energy can be applied to any location within the sonic resonator's acoustic near field, providing sufficient energy to cause controlled change within the biological medium/biomaterial. The resonator system can provide pulse shape, pulse amplitude control, and control of pulse repetition rate to each location to which the localized power pulse is applied. This achieves total spatial peak/temporal average (SPTA) intensity control within the device's acoustic near field. The effect on exposed tissue is typically to break up or shred a cellular structure, rather than destroy tissue by heating or cavitation, as done with conventional sonic systems.

The sonic signal generating system drives the resonator with a specific waveform (from calibration) over a determined period of time. The resonator delivers this sonic energy as a low-level average sonic field that will have a localized phase alignment of the individual frequencies of sound to "reconstruct" a focus in sonic intensity at the location where the calibration acoustic sensing device was located—a "focus-in-time". Multiple electronic signal generators and or resonators may be used to increase the coverage area (interleave mode) or to increase the sonic intensity at a given focal point (simultaneous mode). For biomedical applications, one resonator may have elements which provide both a transmitter and a receiver. The receiver is used to capture backscatter from the biological medium, to determine whether a desired amount of tissue change has occurred. The feedback from the receiver enables the user to control of the number of impulses and the intensity of the impulses, and to initiate a change in the zone (location) of peak intensity to a new location within the sonic near field when appropriate. This is illustrated in FIG. 2, by the various locations 206, within a near field zone 204 in biological medium/biomaterial 203 at which a peak intensity may be placed.

Examples of the broad concepts described above include a sonic resonator system which is used to apply a power pulse at a selected location within a biomaterial, where the system includes: a computer containing software algorithms for signal reconstruction and at least one wave form generator; and at least one sonic resonator assembly in communication with the wave form generator, where the at least one resonator assembly transmits sonic energy into the biomaterial, and where the sonic energy includes at least one power pulse within at least one wave generated using input from the at least one wave form generator. This sonic resonator system typically includes at least one calibration sensor which is used to provide input to the computer/controller, so that the sonic resonator-system may be calibrated to provide a desired outcome in a particular biomaterial. Often the at least one calibration sensor is located in series after the at least one sonic resonator assembly and after a location at which a sample of biomaterial is placed between a sonic resonator assembly and a calibration sensor.

The resonator system needs to be calibrated to work with a biomaterial to which it is applied, to obtain the best results. A typical method of calibrating a sonic resonator system to produce a high intensity impulse, which may be applied as a power pulse at a particular location within a biomaterial, generally includes: providing a sonic resonator assembly which includes a computer/controller containing software algorithms for signal reconstruction and a wave form generator; a sonic resonator assembly which transmits sonic energy into a specified location within the biomaterial in the form of a power pulse; and a calibration sensor. A biomaterial of the kind which is to be treated is placed at a location between the sonic resonator assembly and a calibration sensor. A broadband signal is then constructed in the computer/controller which is used to excite or stimulate an applied voltage signal from the sonic resonator assembly. This broadband signal is applied to the sonic resonator system, which is in communication with said sample of biomaterial, so that a power pulse of a desired shape and amplitude is generated at a location within or at a surface of the biomaterial which faces the calibration sensor. A calibration response generated at the calibration sensor is then measured. A waveform is then generated within the computer/controller, based on the calibration response, where the waveform may be applied to the resonator assembly to produce a high power, wide bandwidth rarefaction power pulse concentrated at a particular location in a biomaterial to be treated.

The general method of applying a power pulse at a particular location within a biomaterial for purposes of treating said biomaterial comprises: providing a sonic resonator system which includes: a computer containing software algorithms for signal reconstruction and a wave form generator; a sonic resonator assembly which transmits sonic energy into the biomaterial, where the sonic energy is in the form of a power pulse; and, a coupling device which couples the sonic energy from the resonator assembly to a location within or at a surface of the biomaterial; and applying a wide-banded high intensity sonic wave which includes a power pulse at a point in time to the resonator assembly, where the time required to traverse a distance within the biomaterial places said power pulse at a selected location within the biomaterial.

Figure 1:
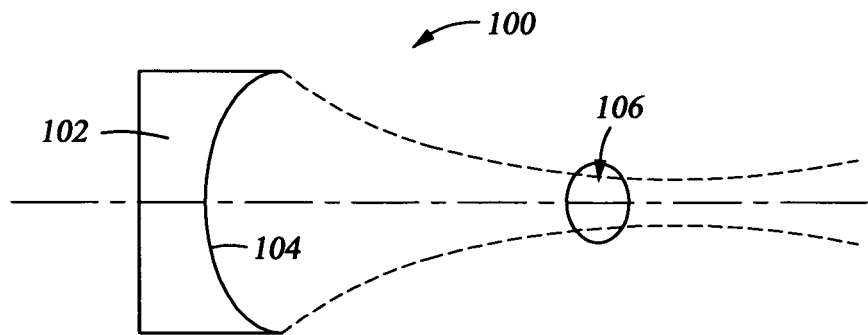
FIG. 1 is a diagram 100 of a prior art system including a transducer 102 shaped to form a spherical lens 104, to produce focused energy at a point in space 106.

During normal operation, sonic backscatter from the biomedium is sensed by the transparent receive piezoelectric assembly 450 and passed via path 454 to the preamplifier 460, A/D converter 470 and finally to the controller 410.

Figure 4A:
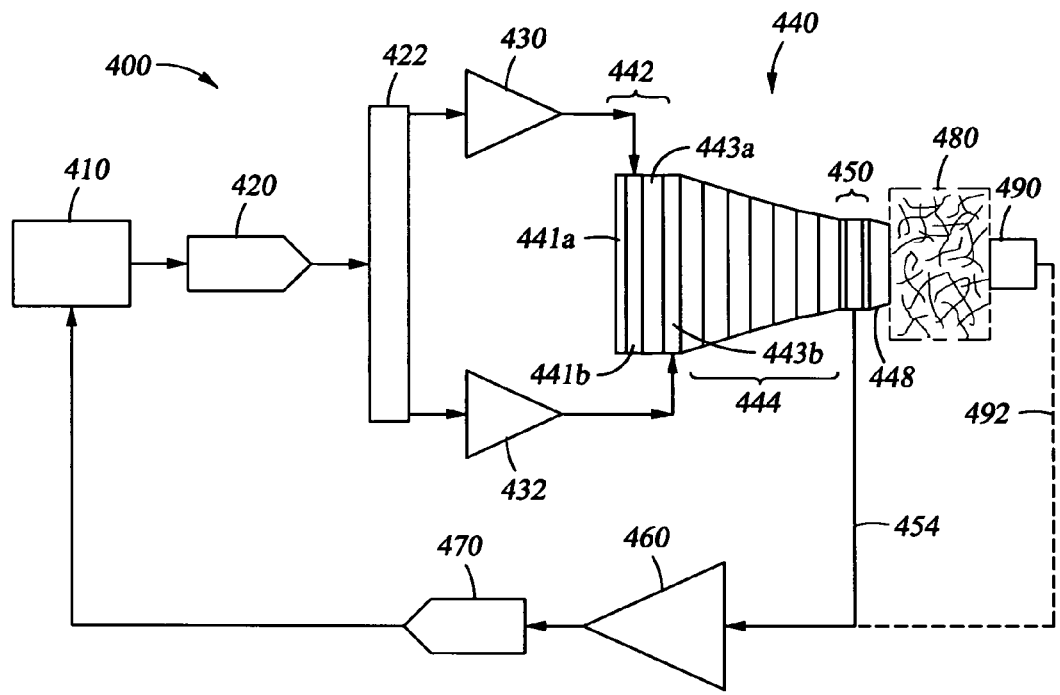
FIG. 4A is a cross-sectional side-view schematic diagram 400 of a typical embodiment of the sonic resonator system of the invention, which includes a controller 410 (typically a computer) which sends signals to a D/A converter 420, which communicates with an input splitter 422, which sends a signal to two power amplifiers 430 and 432, each of which sends a signal to a piezoelectric transducer elements 441*b*, and 443*b*, respectively, which make up a driving transducer assembly 442, as shown in FIG. 4B. The driving transducer assembly 442 is part of a resonator assembly 440, which also includes a lamina of resonator discs in main resonator assembly 444, a transparent receive piezoelectric assembly 450, and a coupling element 448, which couples input from resonator assembly 440 into a biomaterial 480. During calibration, the sonic signal is captured by the calibration sensor 490, and passed via path 492 to a pre amplifier 460, which feeds an A/D convertor 470, which provides a signal to the controller 410.
Figure 4B:
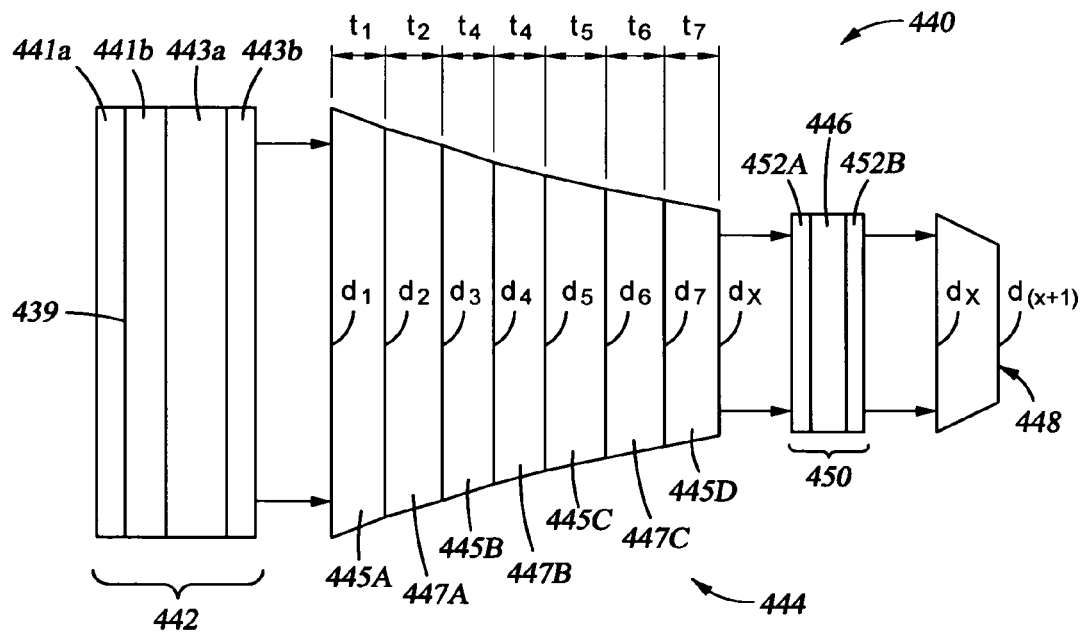

FIG. 4B is an expanded cross-sectional side-view schematic of the sonic resonator assembly 440 shown in FIG. 4A, which is used to illustrate the "taper" of the diameter of the discs in the lamina of discs in main resonator assembly 444 and taper relationships between the driving transducer 442, the lamina of discs in main resonator assembly 444, the transparent receive piezoelectric assembly 450, and the coupling element 448.

Figure 5A:
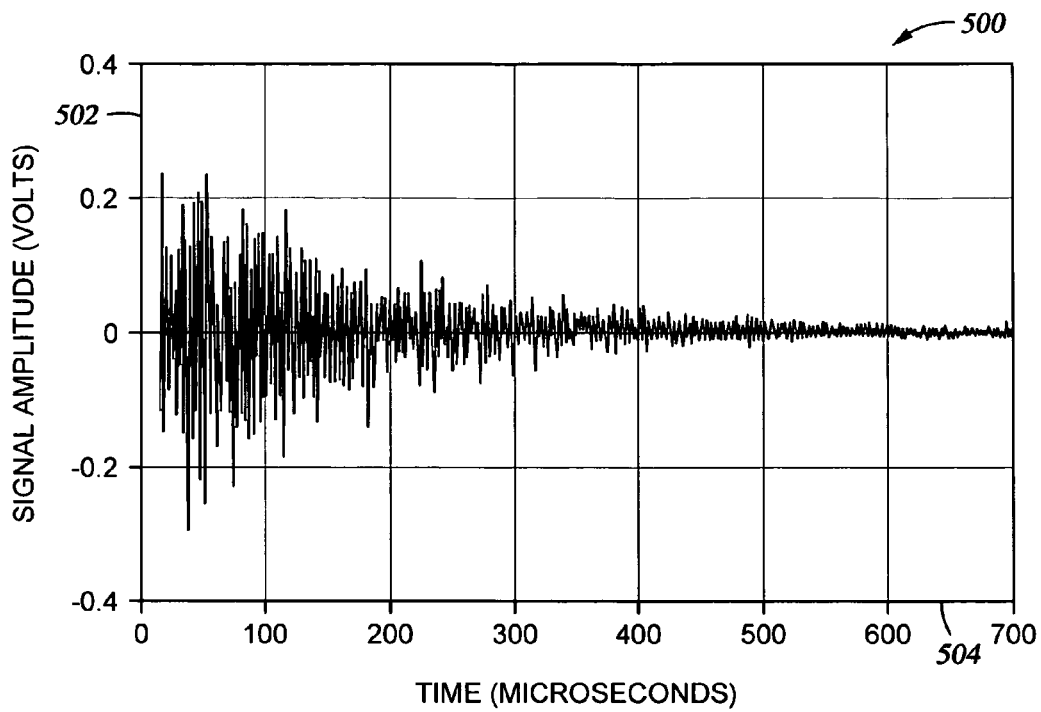
Figure 6A:
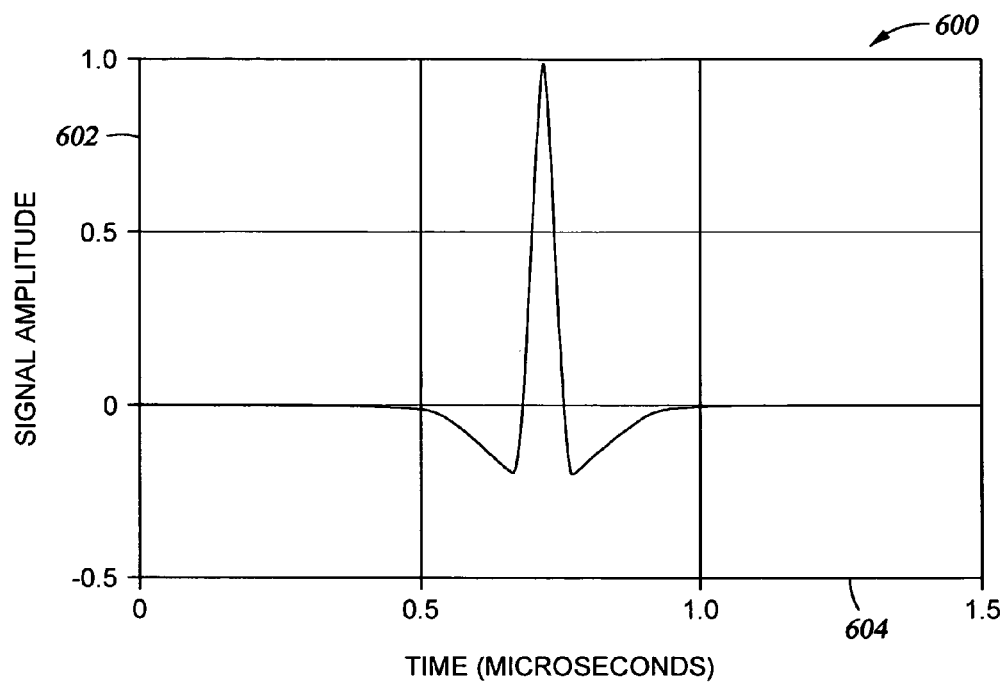

FIG. 5A shows the calibration Capture Waveform, C(t), which corresponds to the Excitation Waveform, I(t), applied in FIG. 6A.

Figure 5B:
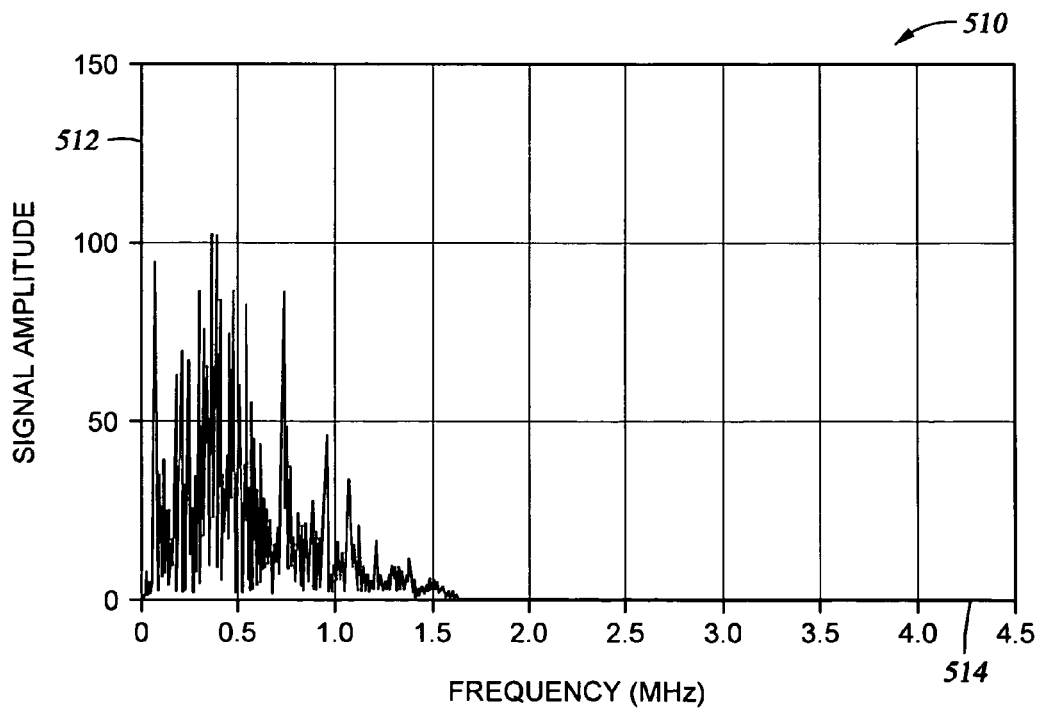

FIG. 5B shows the amplitude and spectral response, $A_C(f)$, which corresponds to the calibration Capture Waveform, C(t), shown in FIG. 5A.

Figure 5C:
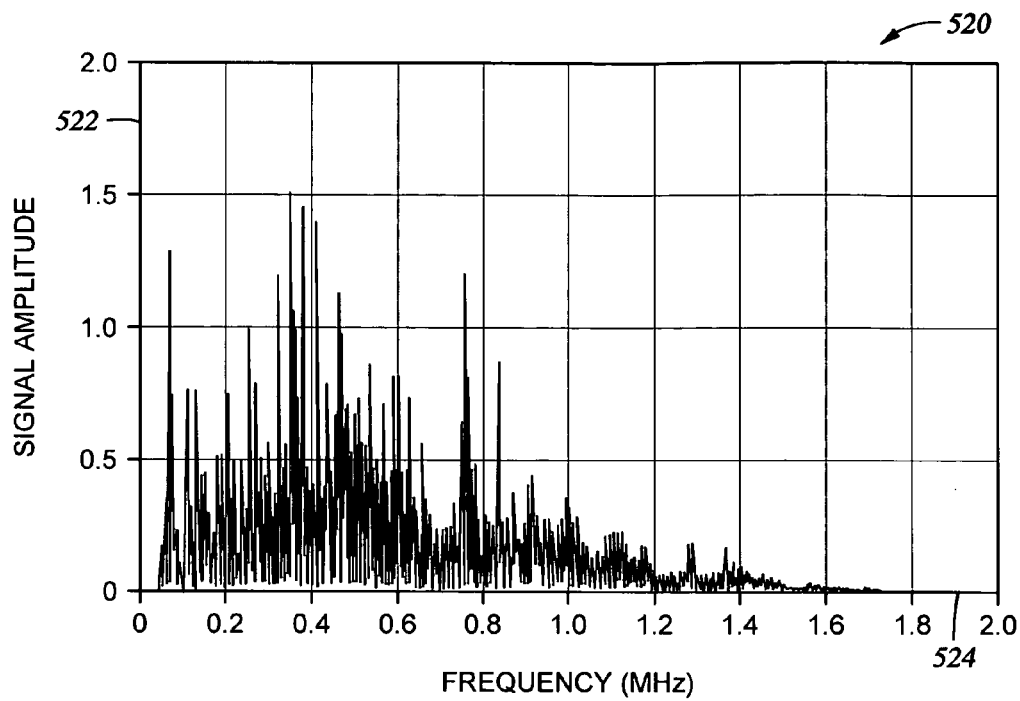

FIG. 5C shows the spectra of the calibration Capture Waveform, $A_C(f)$, expanded for frequency resolution.

Figure 5D:
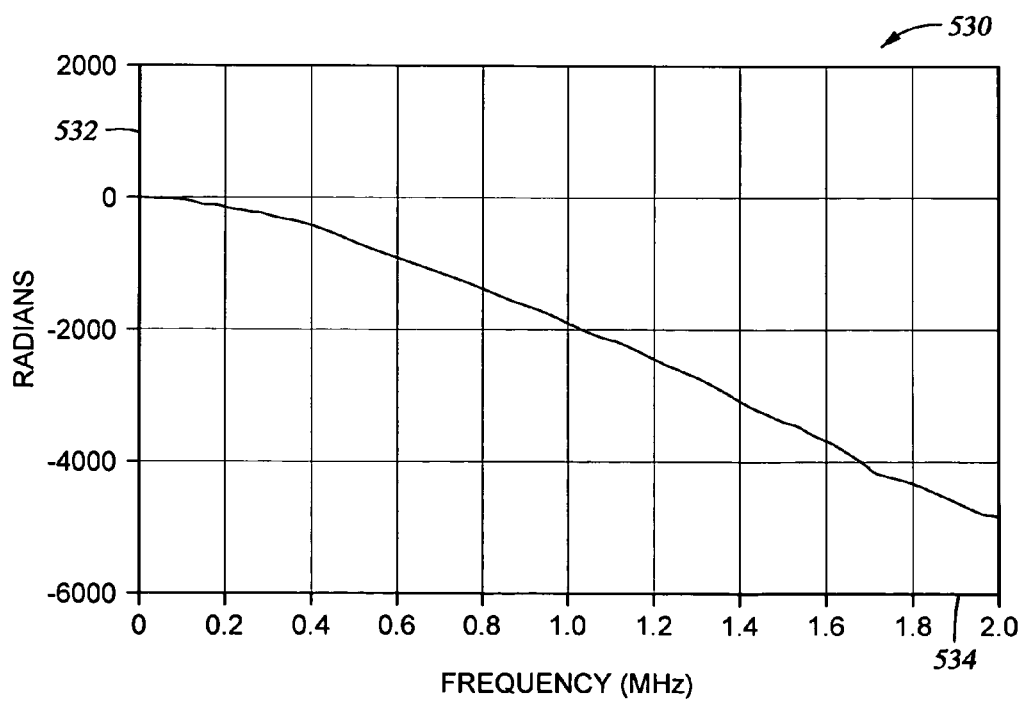

FIG. 5D shows the phase of the calibration Capture Waveform which correlates with the spectra shown in FIG. 5C.

Figure 5E:
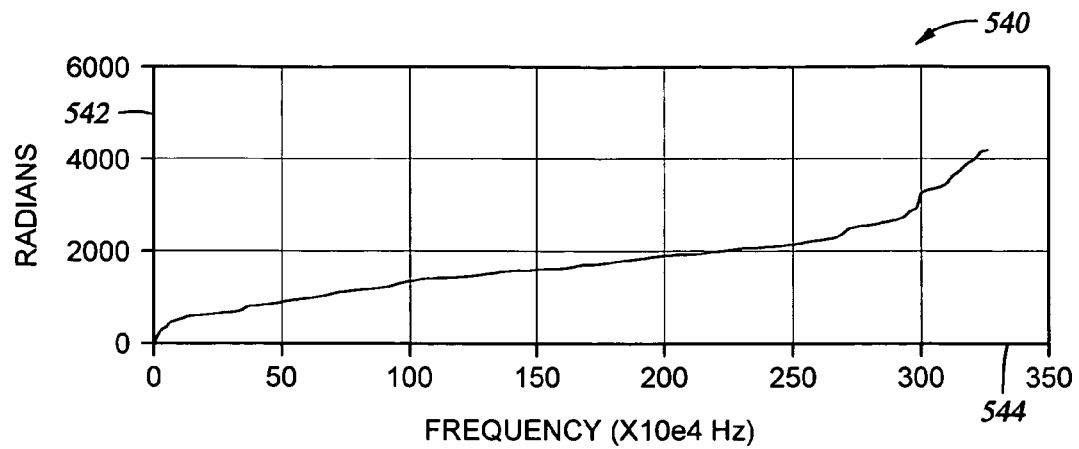

FIG. 5E shows a graph 540 illustrating the raw phase error introduced into the Capture Waveform from the first calibration due to the presence of the biomedical/biomaterial itself. The phase angle in radians is shown on axis 542 as a function of the spectral frequency 544. Note that phase error would be indicated by a line shown from a linear (straight) line.

Figure 5F:
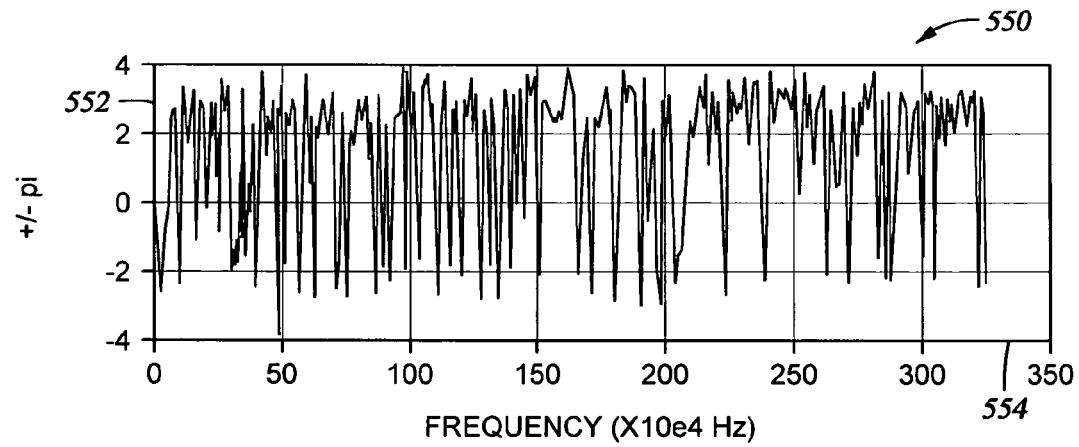

FIG. 5F shows a graph 550 of the phase angle in +/−π on axis 552 as a function of the spectral frequency 554.

Figure 5G:
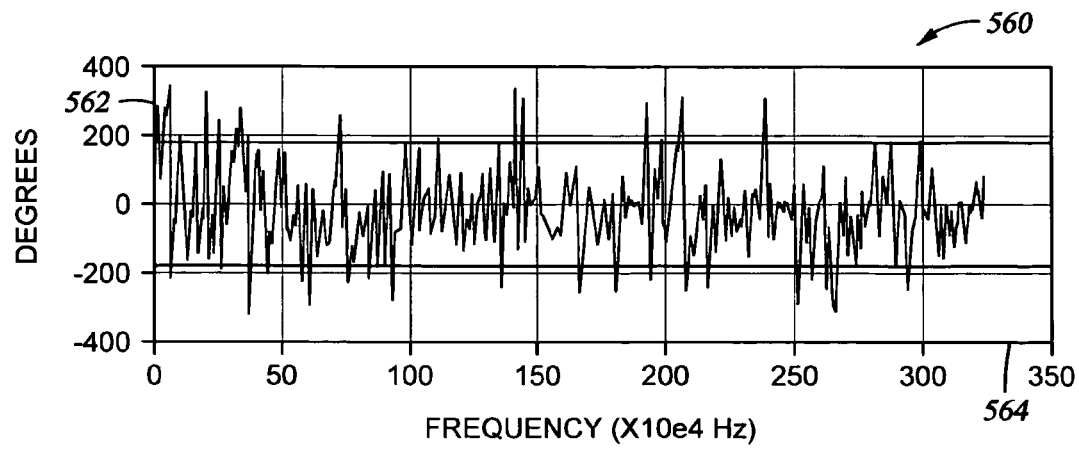

FIG. 5G shows a graph 560 of the phase error correction waveform that will be added to the phase of the Power Packet from the first calibration to create a new phase-corrected Power Packet.

Figure 5H:
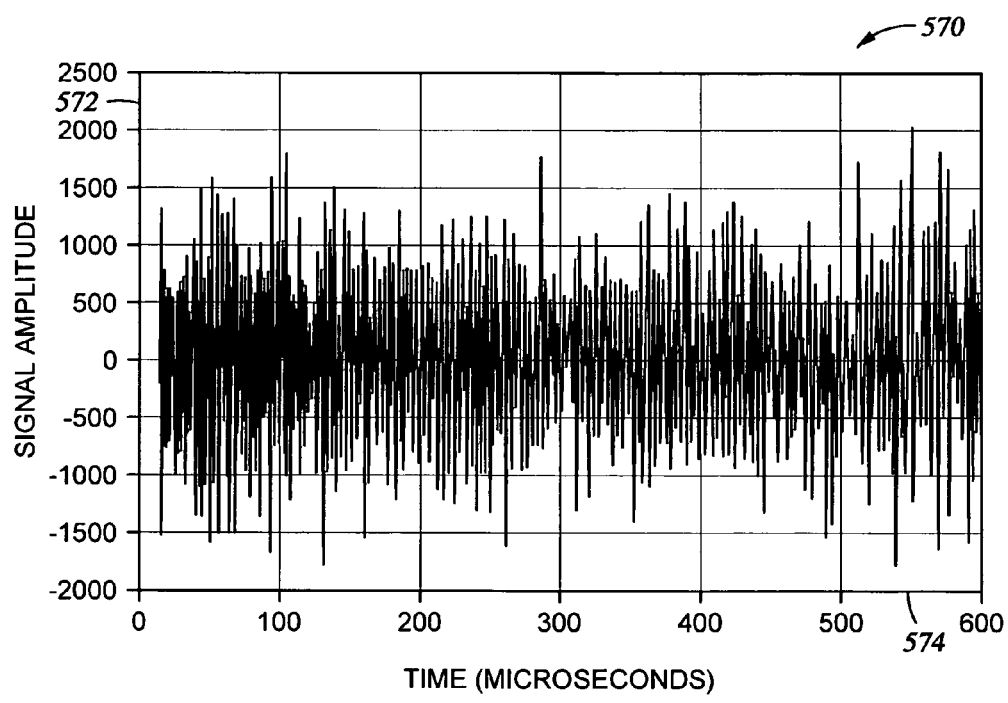

FIG. 5H shows the waveform (Power Packet) 570 which results from the calibration procedure. With reference to the sonic resonator system 400 shown in FIG. 4A, the Capture Waveform is then processed using the calibration software algorithm in computer 410 and passed through D/A converter 420 and power amplifier 430 to the resonator assembly 440 which will produce a high power, wide bandwidth Power Pulse concentrated at the location where the acoustic capture device 490 was present during calibration of the sonic resonator system 400.

FIG. 6A shows a plot 600 showing signal amplitude (in volts) on axis 602 as a function of time (in microseconds) on axis 604 for an applied Excitation Waveform, I(t). In some embodiments of biomaterial testing or treatment, an optimal impulse would be as shown in FIG. 6A.

Figure 6B:
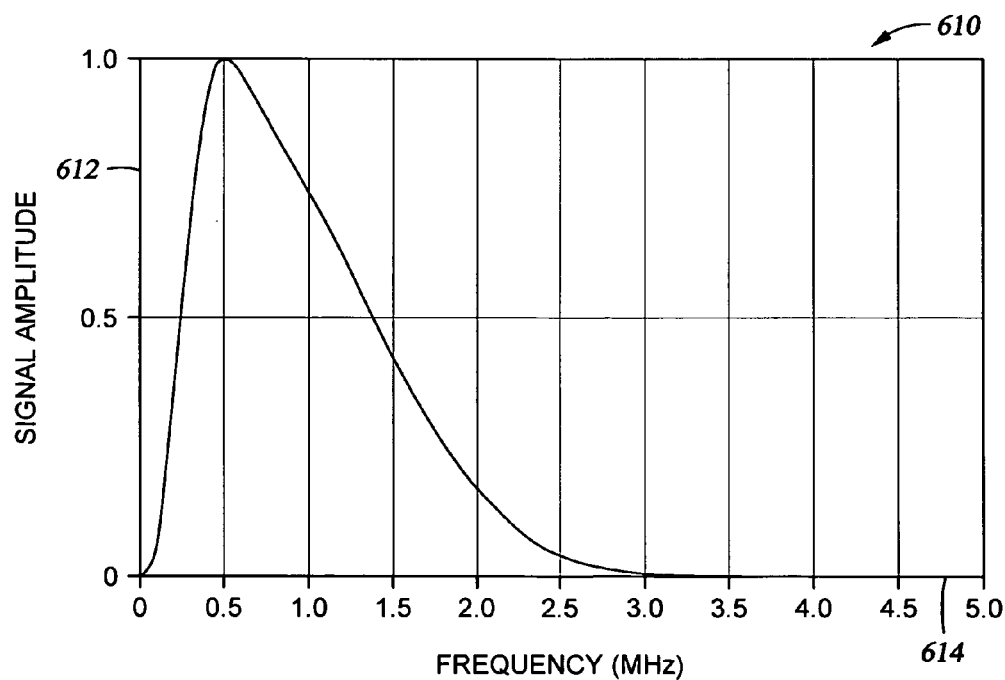

FIG. 6B shows a plot 610 of the Fourier transform signal amplitude, $A_f$, on axis 612 as a function of the signal frequency (in MHZ) on axis 614 for the Excitation Waveform, I(t), illustrated in FIG. 6A.

Figure 7A:
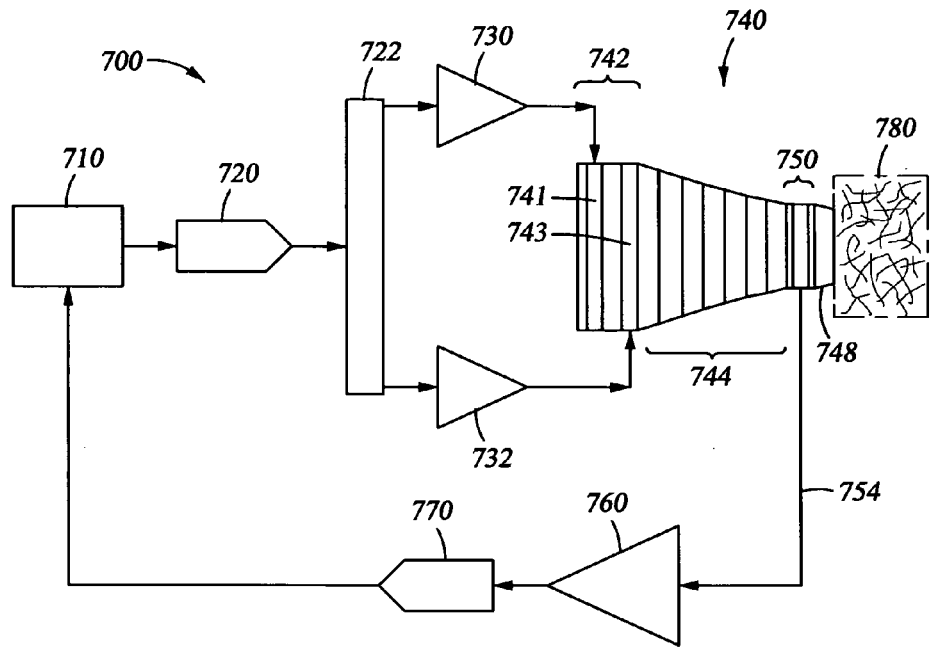

FIG. 7A is a cross-sectional side-view schematic diagram 700 of a sonic resonator system of the kind shown in FIG. 4A, without the calibration elements which are used in calibration mode.

Figure 7B:
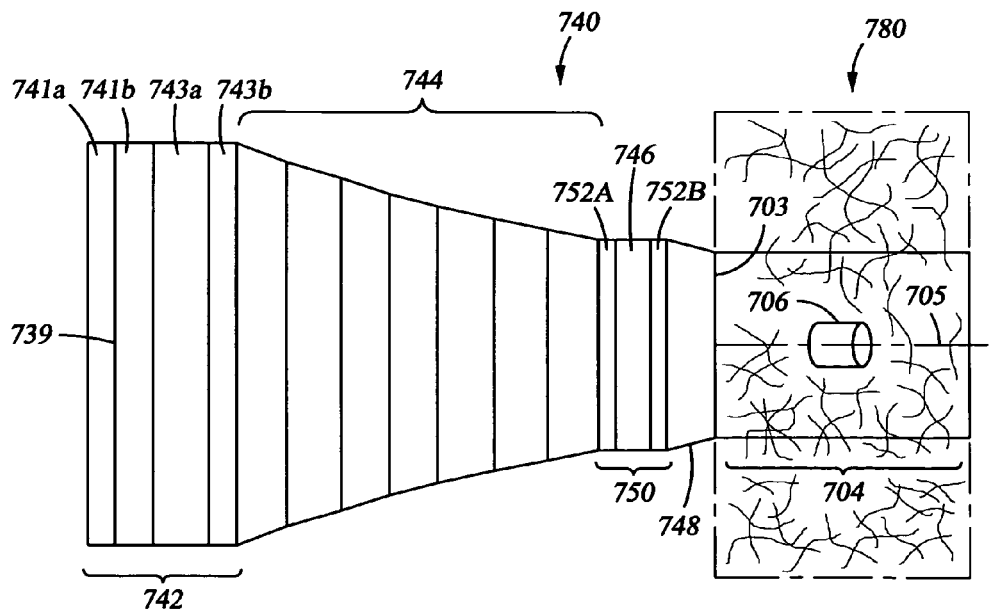

FIG. 7B is an expanded cross-sectional side-view schematic of the sonic resonator assembly 740 shown in FIG. 7A, which also illustrates the near field 704 treatment area of biomaterial 780, with a zone of focused sonic energy 706 present within near field 704.

Figure 7C:
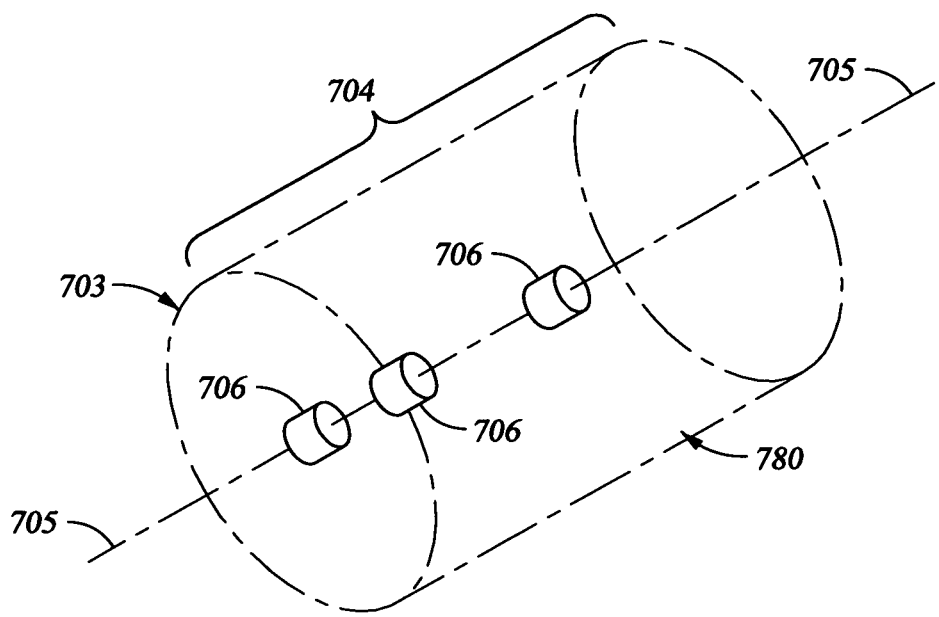

FIG. 7C illustrates oval-shaped focal zones of high-intensity sound pressure 706 created in the biomaterial 780 within near field 704, which high-intensity (focal) zones 706 are created by the multiple outputs from a resonator having a surface area contact 703 with biomaterial 780.

Figure 7D:
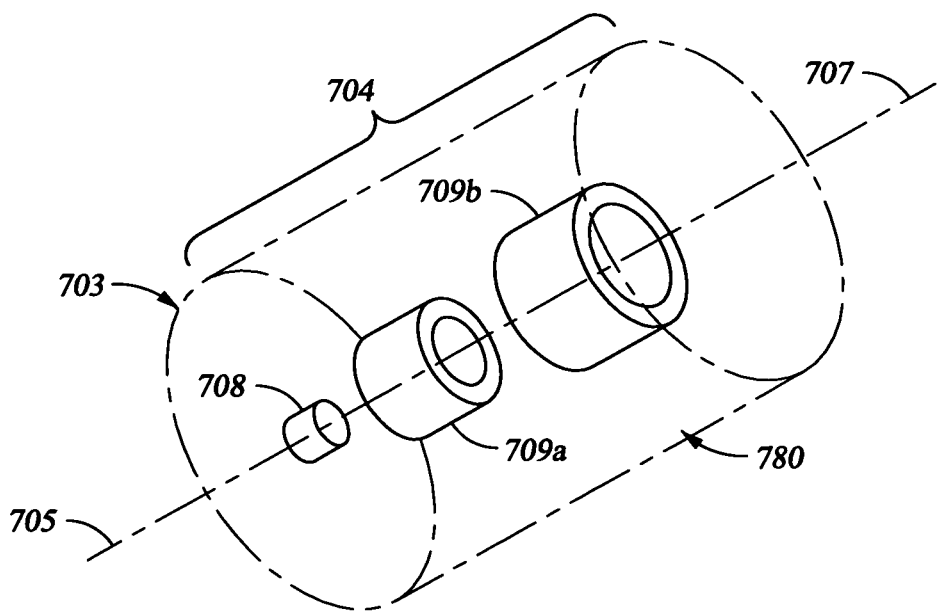

FIG. 7D illustrates off-axis 707 radial zone rings 709a and 709b of high-intensity sound pressure compared with on-axis zone rings 708 created relative to axis 705 illustrated in FIG. 7C. Off-axis calibration sensing can be used to create a larger volume area.

FIG. 8A shows a cross-sectional diagram 800 representing the use of multiple resonator stacks arranged to produce overlapping sonic fields (having axes 802, 804, and 806).

FIG. 8B shows an exterior casing 811 of a dual resonator assembly 810 which includes resonators encased at 812A and 812B, and having a contact area 814.

FIG. 8C shows a cross sectional diagram 820 the dual resonator internal elements 822A and 822B, having contact areas 824A and 824B which are coupled to biomaterial 880.

Figure 9A:
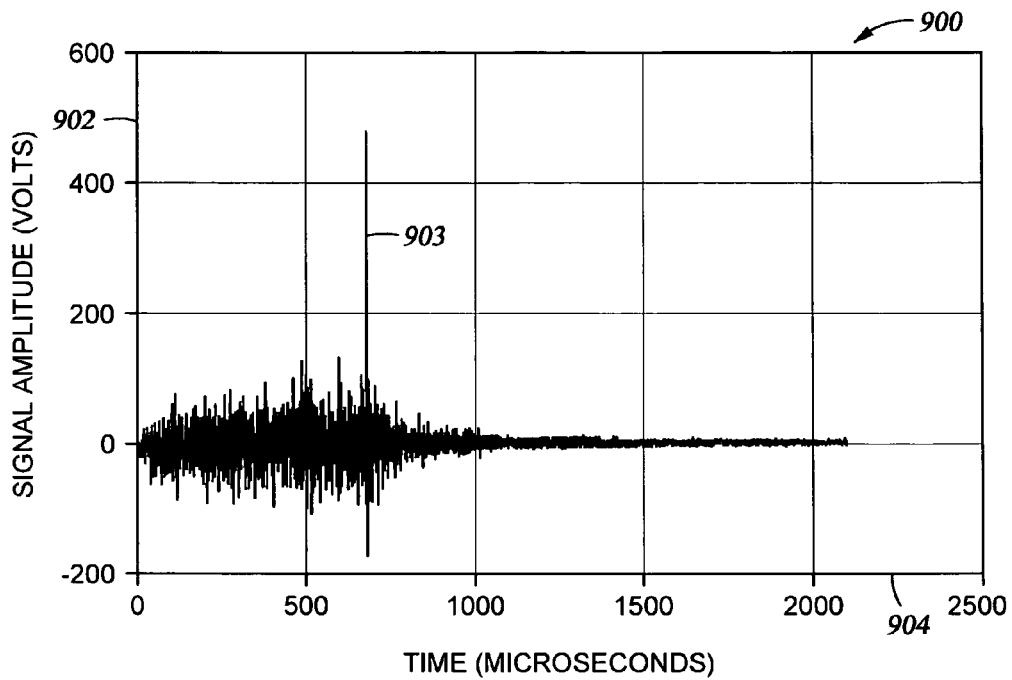

FIG. 9A is an example of an actual Power Pulse created by the sonic resonator of the invention (shown in FIG. 7A) after application of a Power Packet.

FIG. 9A is a plot 900 showing signal amplitude (in volts) on axis 902 as a function of time (in microseconds) on axis 904. FIG. 9A depicts a wide bandwidth compression pulse 903.

Figure 9B:
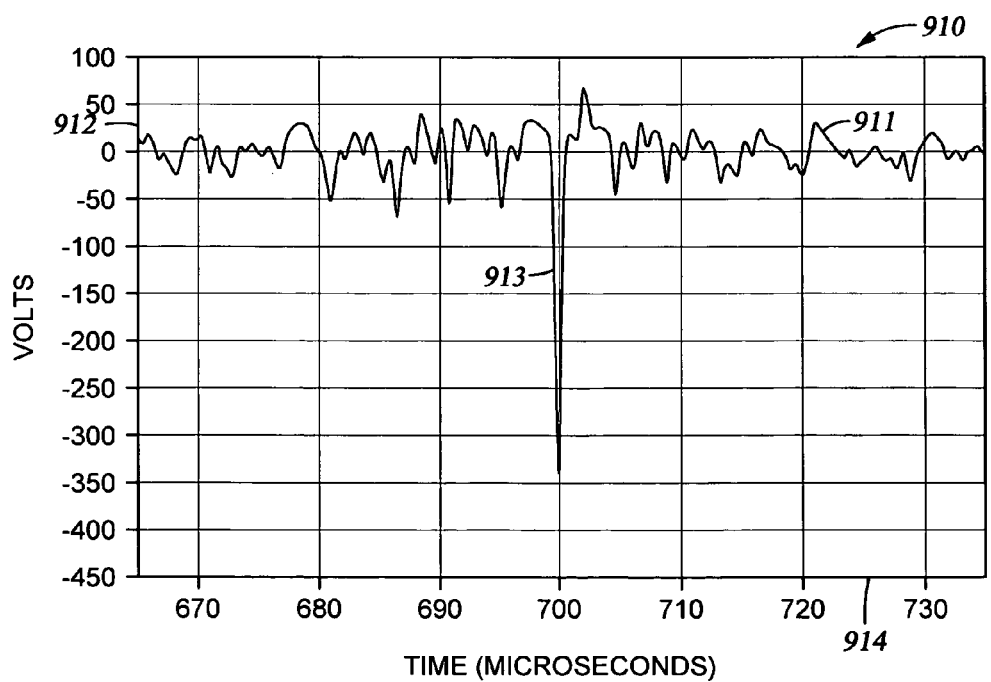

FIG. 9B is another example of an actual Power Pulse created by the sonic resonator system of the invention (shown in FIG. 7A) after application of a Power Packet. FIG. 9B is a plot 910 showing signal amplitude (in volts) on axis 912 as a function of time (in microseconds) on axis 914. FIG. 9B depicts a rarefaction pulse 913.

Figure 9C:
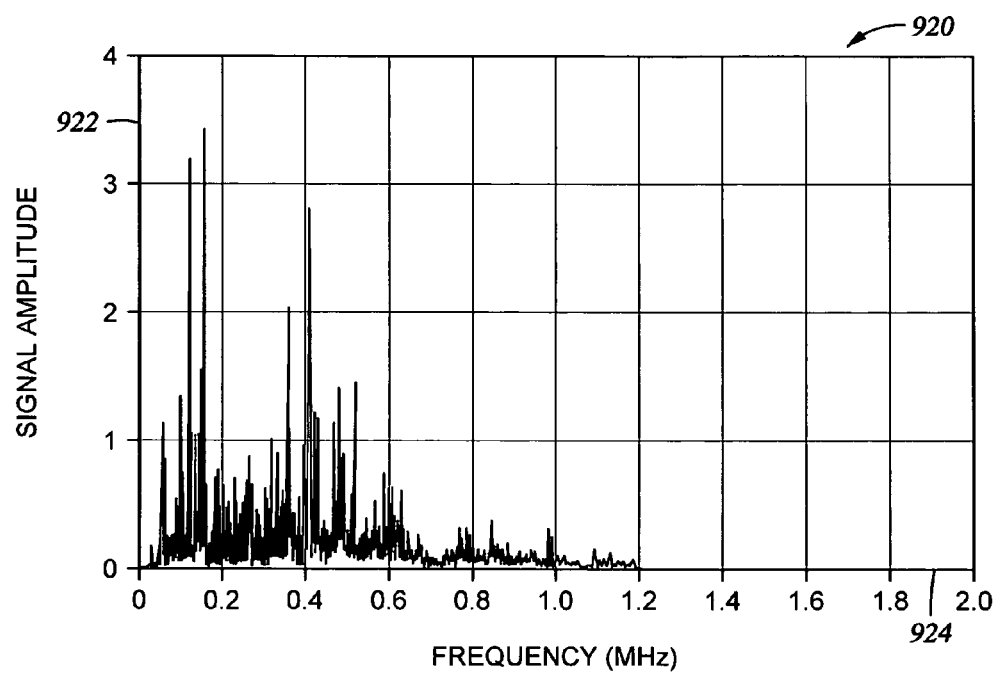

FIG. 9C is a plot 920 showing signal amplitude on axis 922 as a function of frequency (in MHZ) on axis 924, which shows the bandwidth of the compression Power Pulse 903 illustrated in FIG. 9A.

FIG. 10A shows a surface view of a resonator disc 1002 which has a radial kerf 1008 cut into a surface 1003 of disc 1002. The purpose of the radial kerf is to align in time the radial surface wave with the plane wave reverberation in a given disk, to improve the efficiency of the resonator assembly. A number of kerfs (not shown) may be used on a disc surface, depending on the diameter of the disc.

FIG. 10B shows a cross-sectional view of FIG. 10A, illustrating the radial kerf 1008 and the depth and width of the kerf.

FIG. 10C shows a diagram 1020 of the propagation and direction of a plane wave 1022, in combination with radial surface waves 1024 and 1028 which are generated at interfaces 1033 and 1035 in a laminate stack of discs 1032, 1034, and 1036, as the plane wave 1022 passes through the laminate stack. Cutting a kerf of the kind shown in FIG. 10A into the front face of the disc aligns (in time) the radial surface wave with the plane wave reverberation in that disc, so both waves reach an acoustic peak at the same time. Typically, kerfs are cut in selected discs, but may alternatively be cut into each disc. The amplitude of the plane wave diminishes, after passing through the resonator stack, there is less need for kerfs in successive disks in the stack.

DETAILED DESCRIPTION OF EXEMPLARY EMBODIMENTS

As a preface to the detailed description, it should be noted that, as used in this specification and the appended claims, the singular forms "a", "an", and "the" include plural referents, unless the context clearly dictates otherwise.

When the word "about" is used herein, this is intended to mean that the nominal value presented is precise within ±10%.

Embodiments of the invention relate to a method and apparatus for use in therapeutic, cosmetic or aesthetic, diagnostic, exploratory, or other medical procedures. The methods of use are far less invasive than other methods of treatment which might be used.

Figure 2:
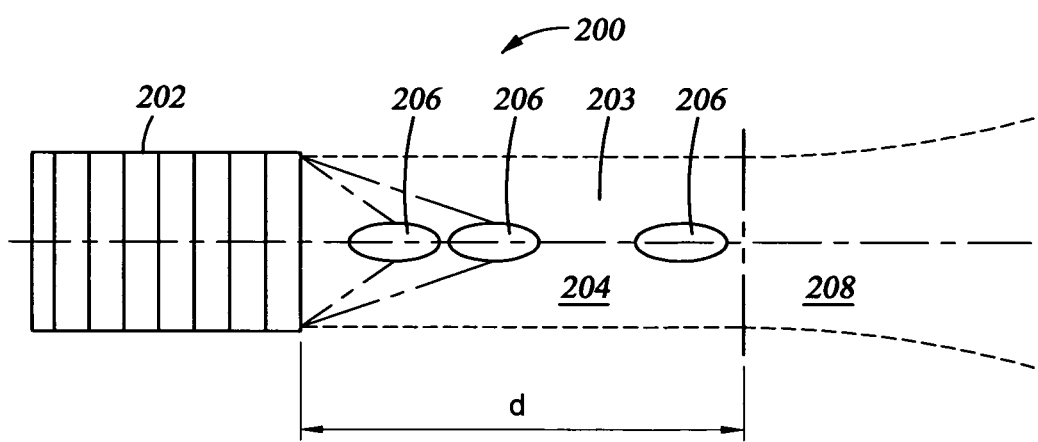
FIG. 2 illustrates the "focus-in-time" concept which is the basis of embodiments of the present invention. Shown in FIG. 2 is a schematic diagram 200 of a resonator 202 which is coupled to a biomaterial 203 in a near sonic field 204. The resonator 202 delivers multiple zones of high intensity sonic impulses 206 into the near field 204 (as distinguished from far field 208).

FIG. 2 shows a schematic diagram 200 of a resonator. 202 which is coupled to a biomaterial 203 with a resulting near sonic field 204. The resonator 202 delivers multiple zones of concentrated (focused) acoustic intensity 206 into the near sonic field 204. The sonic resonator system overcomes the disadvantage of conventional fixed focal depth devices in that it does not need to have a standoff between a transducer used to generate an acoustic input and the surface of a biomaterial (biomedium) to permit change in depth of focus. Instead, the waveform transmitted into a transducer (not shown) which drives the resonator is manipulated during the calibration procedure to cause a localization of concentrated sonic energy (focus) at any selected location within the low average power, sonic near field 204. Due to the typical beam spreading in the acoustic far field 208, the acoustic energy quickly diminishes once the far field is reached. Further, use of a sonic resonator 202 enables delivery of a much lower average power, when desired, so that temperature rise in a biomaterial 203 can be maintained within an acceptable range during application of a high intensity sonic impulse (a power pulse).

The strength of the acoustic intensity at a "focal" localization of a power pulse is typically greater than 20 MP (Mega Pascal), lasting for a very short time duration, typically about 1 microsecond. This high acoustic energy can be "concentrated" at any location within the acoustic near field of a sonic resonator assembly of the type which will be described below. The focused energy (power pulse) produced can cause controlled change within a biomaterial. The sonic resonator system of the invention can provide a pulse shape, pulse amplitude control, and control of pulse repetition rate to each of a number of locations within a biomaterial. This may be referred to as total spatial peak/temporal average (SPTA) control within the device's acoustic near field. An important advantage of the sonic resonator system of the invention is that it delivers very high peak sonic intensities (which may be sonic compression or rarefaction), which is quite different from continuous wave devices of the kind used in the past. The key advantage over the continuous wave systems is that the effect of the sonic power pulses is to break up or shred cellular tissue without heating up the biomaterial in general. The effect is local and the action is rapid in time period.

The apparatus and method of the invention may make use of multiple generators/resonators to increase the coverage area to which sonic energy may be applied (interleave mode), or to increase the sonic intensity for specific locations (simultaneous mode). It is possible to use one of the resonators to act as both a transmitter and a receiver (transducer) to capture the backscatter from the biomaterial and to capture the backscatter for determination of change within the biomaterial. If more than one resonator is used, only one needs to have a (transparent) receive capability. Use of the backscatter information from the biomaterial enables control of the number of power pulses applied and may be provided to an analysis and control system which enables automatic moving of the zone of peak intensity (focus) to a new location within the sonic near field.

Mathematical Analysis

It is well-known that most systems can be understood and analyzed in either the frequency or time domain. Both domains will be used in describing the present invention. Either method could be used, but the use of both provides nuances that illustrate various aspects of the invention. The following mathematical analysis establishes the design requirements for the sonic resonator assembly and the calibration procedure:

Consider a voltage signal V(t) for the time t between 0 and T. This can be represented by a discrete series of n voltages $V_i$, where:

$$V_i \geq V(i\Delta t) I=0,1,\ldots,n$$

and $$n=T/\Delta t$$

A. Frequency Domain Analysis

The discrete Fourier sine transform of this signal is:

$$a_i = \Sigma_j V_j \sin(2\pi ij/n)$$

And the cosine transform is:

$$b_i = \Sigma_j V_j \cos(2\pi ij/n)$$

And the amplitude transform is:

$$A_i = \sqrt{a_i^2 + b_i^2}$$

And the phase transform is:

$$\theta_i = \tan^{-1}(a_i/b_i)$$

The signal is completely defined by either $a_i$ or $b_i$ or by $A_i$ and $\theta_i$, that is, given either set of numbers, the original signal can be calculated by the inverse Fourier transform. These operations (the Fourier and inverse Fourier transforms) are operations supported by practically all computer languages that are used for mathematical operations, and will not be further defined in this invention. It will be convenient to use the amplitude and phase rather than the sine and cosine representation of the Fourier transforms in the following discussion.

Consider a system (such as the sonic resonator of the present invention) that produces a phase shift of each frequency component of the input signal by some measurable amount $\theta_s(f)$. Suppose that it is desired that the output signal be an impulse at some specific time T and phase $\theta_o$, i.e., a signal with a linear phase transform with a specific slope:

$$\theta_d(f) = kf + \theta_o$$

where:
k=slope=$2\pi T$
$\theta_o$=phase of the desired impulse
T=time when the impulse occurs The phase transform $\theta_a(f)$ of the signal when applied to the resonator that will produce this impulse is:

$$\theta_a(f) = \theta_d(f) - \theta_s(f) + \theta_o$$

In order to take the inverse transform to define the applied signal, an amplitude transform is required. A large variety of wide band functions can be used. Some suitable functions will be discussed below.

B. Time Domain Analysis

The present invention can be understood by analysis in the time domain, i.e., requiring no Fourier transforms. The general approach is to imagine the transducer transmitting an impulse function (a Dirac delta function) into the resonator and finding the response. This can be convolved with the transmitted function to find the actual response.

The Dirac delta function is defined as follows:

$$\delta(t-t_o) = 0 \text{ if } t \neq t_o$$

=A special kind of infinity if $t=t_o$
It is special in that:

$$\int_A^B \delta(t-t_o) dt = 1 \text{ if } A \leq t_o \leq B$$

=0, otherwise, and $\int_A^B f(t)\delta(t-t_o)dt = f(t_o)$ if $A \leq t_o \leq B$ =0, otherwise.

The theoretical response, R(t) of the resonator to an input impulse function δ(t) can be written as follows:

$R(t) = \Sigma_i A_i \delta(t-t_i)$ where:

$t_i$=the output time of the $i^{th}$ reverberation, and $A_i$=the amplitude of the reverberation.

The practical consequence of this is that the drive function can be obtained as follows:

1. Drive the transducer-resonator with some impulse function, I(t).
2. Measure the system response, R(t).
3. Time reverse the system response, R(T−t).
4. Normalize R(T−t) by multiplying it by a smooth function. Normally, the amplitude of the response decays by $\epsilon^{-t}/Td$, so multiplying R(T−t) by $\epsilon^{+t}/Td$ results in a function $f(t)$ which is uniform in amplitude from t=0 to T.
5. Drive the resonator with $f(t) = \epsilon^{+t}/Td * R(T-t)$.

The result is an impulse out of the resonator at t=T. This demonstrates how the drive function may be obtained by analyzing the system in the time domain. A high amplitude impulse can be generated by using a drive function which is the time-reversed drive function normalized to the sum of constant amplitude delta functions:

$D(t) = \Sigma \delta(T-t) \text{sign}(A_i)$

The sign $A_i$ is provided because $A_i$ may be positive or negative, so the normalized drive function has delta functions that have amplitudes of either +1 or −1.

The system response to this is then:

$R_A(t) = \Sigma_i \Sigma_j |A_i| \delta(T-t_j+t)$

Note that when i=j, $R_p(t) = \Sigma_i |A_i| \delta(T)$

In other words, the amplitude at T is the sum of all the echoes, whereas at other times of $t_i - t_j$, the amplitude is just $|A_i|$. The actual output is $R_p(t)$ convolved with the actual drive function.

Concept of the Present Invention

Figure 3A:
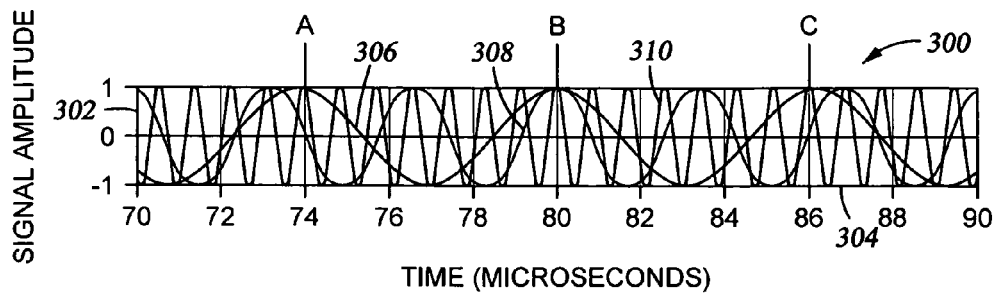
FIG. 3A illustrates that multiple individual cosine waves (for example and not by way of limitation) can be aligned using the calibration procedure and algorithms of the invention, a combination of the waves provides a Power Pulse (peak) at a particular point in time. Illustrated at point B in FIG. 3A.
Figure 3B:
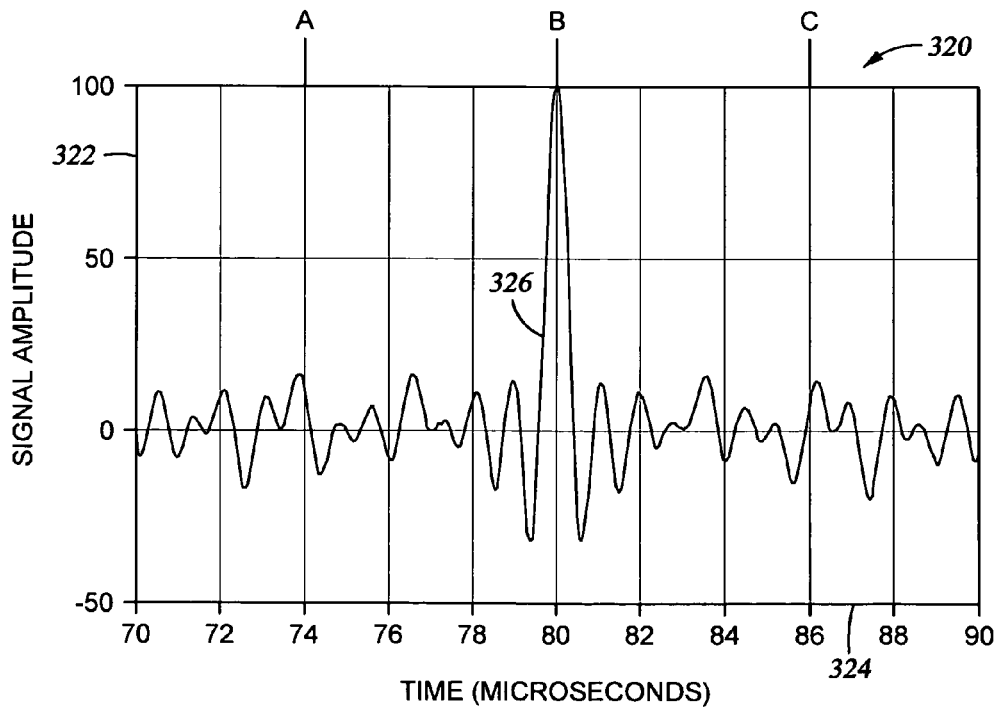
FIG. 3B illustrates the summation of the amplitude of the waves shown in FIG. 3A at each point in time between 70 microseconds and 90 microseconds. A power pulse occurs at 80 microseconds, when the three cosine waves shown in FIG. 3A align at their maximum amplitudes to provide a maximum summation amplitude.

FIGS. 3A and 3B illustrate one basic concept behind the apparatus and method of the invention. FIGS. 3A and 3B show graphs 300 and 320, respectively which illustrate that multiple individual cosine waves (by way of example and not by way of limitation) can be aligned using a calibration procedure with the biomaterial to be treated, and an algorithm which is part of the invention, such that a wave peak is created at a particular point in time. Lines A and C on FIG. 3A illustrate points (at 74 and 86 microseconds, respectfully) where the maximum amplitudes, as illustrated on axis 302 of the three cosine waves (306, 308, and 310) shown on the figure are somewhat misaligned in time, as illustrated in microseconds on axis 304. Line B on FIG. 3A illustrates the point (at 80 microseconds) where the maximum amplitudes of all three of the cosine waves converge to provide a wave peak or high intensity impulse at this point in time. This results in a magnified amplitude pulse B at a very specific point 326 in time (in this case, 80 microseconds) shown in graph 320 of FIG. 3B. FIG. 3B represents a summation of all the waves shown in FIG. 3A, and illustrates what is meant by the "focus-in-time" concept on which a portion of the present invention is based. This "focus-in-time" allows a high amplitude (illustrated on axis 322) pulse of sonic energy to be delivered to a target tissue at a very specific point 326 in time (illustrated on axis 324) which, as described above, prevents significant heating of the tissue and/or collateral damage to adjacent tissues.

An Exemplary Sonic Resonator System

FIG. 4A is a diagram showing one embodiment of a sonic resonator system 400 of the invention, with the system 400 shown in calibration mode. With reference to FIG. 4A, sonic resonator system 400 includes a sonic resonator assembly 440, which transmits sonic energy into a sample of a biomaterial 480 to be diagnosed or treated, for example. A computer/controller 410 contains software algorithms that construct the appropriate digital signal that is then applied to a digital-to-analog (D/A) converter 420. The D/A converter 420 may be connected directly to a power amplifier (not shown), or may be connected to an input splitter 422, which is connected to a plurality of power amplifiers (as illustrated in FIG. 4A) when there are a plurality of transducers (441b and 443b) used to provide input to the sonic resonator assembly 440.

As illustrated in FIG. 4A, an input splitter 422 communicates with power amplifiers 430 and 432. Power amplifier 430 communicates with driving transducer 441b (also shown in FIG. 4B), and power amplifier 432 communicates with driving transducer 443b. Driving transducers 441b and 443b provide within to sonic resonator assembly 440. Sonic resonator assembly 440 also includes a transparent receiver transducer assembly 450, which comprises transducer 446 which is sandwiched between metal discs 452A and 452B. A coupling element 448 is typically used to couple the signal from a sonic resonator assembly 440 to a biomaterial 480.

During the calibration procedure, an acoustic capture device (sensor) 490 is used to capture the response of the application of an excitation waveform (FIG. 6A) as it is observed in a biomaterial 480. The capture waveform (FIG. 5A) is a result of input of a wideband acoustic impulse of the kind illustrated in FIG. 6A which has been applied to a biomaterial 480 by resonator assembly 440. The capture waveform data gathered by the acoustic capture device 490 includes the necessary phase information for each frequency generated by the resonator, which is unique to the location where the acoustic capture device is located. The input resulting waveform captured by calibration sensor 490 is passed through a pre-amplifier 460, through the A/D converter 470 to the computer/controller 410. The computer/controller 410 processes the waveform to create a power packet waveform to be applied to the resonator to create a high acoustic intensity impulse (FIG. 9A) at the location where the acoustic capture device was located. The waveform generated by the computer/controller 410 can then be changed to provide an adjusted acoustic impulse and an adjusted power pulse into the biomaterial 480, which is particular to that biomaterial. The details of the signal capture process and analysis (calibration) will be described in detail below, under the heading "Method of Calibrating the Sonic Resonator System".

The piezoelectric receiver 450 (which is typically transparent during transmit), which is integral to the sonic resonator assembly 440, is used during normal operation of the system to provide feedback to the user about the effect of a treatment of biomaterial. During clinical procedures, the piezoelectric receiver 450 is connected to the computer through a pre-amplifier 460 and A/D converter, as illustrated by pathway 454 in FIG. 4A.

FIG. 4B is an expanded side-view schematic of the sonic resonator assembly 440 shown in FIG. 4A. The sonic resonator assembly 440 can be broken down into four sub-assemblies, as follows:

1. A dual piezoelectric driver assembly 442 comprising a pair of commercially available piezoelectric elements 441b and 443b, each of which is individually driven by its own power amplifier (not shown) to provide waveforms into the main resonator assembly 444.

2. The main resonator assembly 444 comprises alternating lamina of discs (445, 447) having different acoustic impedances Z.

3. A transparent receiver assembly 450, including piezoelectric element 446 that acts as an additional resonating disc during transmit, and as a receiving element at other times.

4. A coupling element 448 for coupling the main resonator assembly 444 to the biomaterial 480.

With reference to FIG. 4B, the resonate frequency and size (diameter) of the piezoelectric elements is chosen based upon the biomaterial to be treated and the maximum depth of the near field. Standard commercial piezoelectric elements are available from various suppliers, such as, for example, Keramos Advanced Piezoelectrics, available from Channel Industries, Santa Barbara, Calif., and piezoelectric elements available from Piezo Technologies, Indianapolis, Ind. Some typical examples of piezoelectric element materials of interest include Lead Zirconate Titanate (PZT), Lead Titanate (PT), and Lead Metaniobate, which has the lowest acoustic impedance of all the piezo-ceramics.

The pair of piezoelectric driver elements 441b and 443b are separated by a metallic disc 443a which has an acoustic impedance lower than that of driver element 441b, where the impedance ratio of the driver element 441b to the metallic disc 443a ranges from about 1.3:1 to 2.5:1. Aluminum is typically a good choice for metallic disc 443a. The thickness of disc 443a needs to be matched to the one-way flight time of sound through the piezoelectric, or ½ of the wavelength of the piezoelectric driver element (441b or 443b). The dual piezoelectric drive assembly 442 may be further optimized if the two piezoelectric elements are equally 'loaded'. This is achieved by having the piezoelectric driver element 441b backed with a metallic disc 441a which has the same acoustic impedance as the disk 443a which is used between the elements, in this example, aluminum. The effective thickness of the 441a disc (in flight time) is selected to enhance or to be compatible with the other discs in the resonator assembly.

It is helpful to refer to the thickness of the discs in the resonator stack by reference to the wavelength ($\lambda$) of the piezoelectric driver element. For example, the piezoelectric element's thickness is ½$\lambda$. (or its one way flight time), times the velocity of sound in the piezoelectric material. Referencing to $\lambda$ allows for scaling the lamina of disc thickness as a function of the resonant frequency of the piezoelectric element, and allows for the thickness of each disc per its characteristic sound velocity.

In one preferred embodiment, the effective thickness of disc 443a is ½$\lambda$. A piezoelectric dual driver assembly consisting of elements 441a, 441b, 443a, and 443b, for example, often comprise discs which may be of a selected diameter depending on the application, (the surface area of contact desired or available with reference to a biomaterial 480). An exemplary diameter range may be between 0.5 inch and 3 inches in diameter. The resonating characteristics of the alternating lamina of the resonator discs 445 and 447 which make up the main resonator assembly 444 are matched to the frequency of the piezoelectric driver elements. Typically, each of the discs in the main resonator assembly 444, other than the disc which is closest in proximity to the driver piezoelectric element, have the same thickness, which is 1$\lambda$. The first main resonator disc, next to the last driver piezoelectric 443b in the sonic flow path is typically ¾$\lambda$. For example, in FIG. 4B, disc 445A would have a thickness of ¾$\lambda$, and the remaining discs 447A through 445D would have a thickness 1$\lambda$. The total receiver assembly 450 would have a thickness of 1$\lambda$. The transparent receiver assembly behaves as an additional resonating disc, and must have the proper thickness and maintain the 1.3:1 to 3:1 impedance ratio discussed in more detail subsequently herein. The transparent receiver assembly 450 (including all three elements) when present, is ratioed with respect to the disc immediately before the assembly, and with the coupling element 448 immediately following the transparent receiver assembly.

One of skill in the art of piezoelectric driver elements can select an estimated piezoelectric material frequency and size for a given biomaterial to be treated, followed by a preliminary evaluation following the calibration method described herein, and then adjust the frequency, diameter, and thickness of the piezoelectric driver element to optimize the piezoelectric driver element for a particular biomaterial.

In one embodiment illustrated in FIG. 4B, the main resonator assembly 444 comprises alternating metallic discs (445, 447) having different acoustic impedances (Z). Suitable materials might be aluminum for low Z discs 445 ($Z=17\times10^6$ Rayls in MKS units (kg/m²-sec)), and copper for high Z discs 447 ($Z=43\times10^6$ Rayls). A typical main resonator assembly might have between five and seven alternating discs, beginning with aluminum as the first main resonator assembly disc, following the piezoelectric driver assembly 442. All of the metallic discs except the first one, 441a, which precedes piezoelectric element 441b, are machined to have a precise thickness (determined by the acoustic velocity characteristic for the metal). Disc 441a is a backing disk and is optionally present. In addition, the entire dual driver assembly 442 may be replaced with a single piezoelectric driver.

Materials with impedances similar to Piezoelectrics which are suitable for use in the present invention include copper, brass, and Kovar® (a nickel-cobalt ferrous alloy), for example and not by way of limitation. Low acoustic impedance materials suitable for use in the present invention include aluminum, tin, titanium, and indium, by way of example and not by way of limitation. High acoustic impedance materials suitable for use in the present invention include nickel, platinum, gold, and molybdenum, by way of example and not by way of limitation.

With reference to transparent, receiving piezoelectric assembly 450, the metallic discs 452A and 452B, which are in close proximity to the receiving piezoelectric element 446, as illustrated in FIG. 4B, typically have an effective thickness which is thinner (shorter flight time) than the other discs in the lamina of discs, in order to provide optimal flight time between the total transparent receiving piezoelectric assembly 450 and the resonator discs in the main resonator assembly 444. For example, discs 452A and 452B typically have an effective thickness of about ¼ lambda.

The amplitude coefficients of the reflected R and transmitted T acoustic waves at each interface of the lamina are:

$$R = \frac{Z_1 - Z_2}{Z_1 + Z_2}$$

$$T = \frac{2Z}{Z_1 + Z_2}$$

Where: $Z_1$=Impedance of material containing the wave before the interface; and $Z_2$=Impedance of material containing the wave after the interface.

The reflection coefficient may be negative, in which case a negative impulse is reflected. If the difference in impedance between the lamina were near zero, there would be no acoustic reverberation, that is, the input signal would travel to the output with little energy retention. On the other hand, if there is too large a difference in impedance between the lamina, the signal would reverberate so many times that it would attenuate (i.e., turn into heat) before emerging.

Impedance ratios within the range of 1.3:1 to 3:1 and, more typically, within the range of 1.5:1 to 2.5:1 are suitable, although a much wider range is usable. Examples of metals which have desirable characteristics for machining and which can be used in combination to provide impedance ratios within a range of about 1.3:1 to 3:1 between pairings are, for example, copper:aluminum; brass:aluminum; Kovar:aluminum; and molybdenum:titanium. If the attenuation coefficient of the material is low (like titanium), higher reflection coefficients can be used because the wave can reflect a greater number of times without excess attenuation.

It might seem that having multiple discs of the same thickness would produce a strong resonance. There is only one path from the piezoelectric driver assembly 442 to the output through coupling element 448; however, that signal is weak because of all of the reflections from the number of reflective interfaces along the way from the piezoelectric driver element 442 to the coupling element 448. In the entire resonator assembly 444, which comprises seven resonating elements, there are 45 paths with two reflections; 1695 paths with four reflections; and over 10,000 paths with six or more reflections, from the piezoelectric driver element 443 to the output.

This multitude of reflections results in "resonances" at a wide range of frequencies; in other words, a broad band resonator. The adhesive bonds between the lamina must be strong to withstand the high stresses produced by the resonating build-up of sonic energy, especially near the output end of the reservoir. Low viscosity two-part adhesives typically have sufficient bond strength, but if not, the discs can be bonded using a vacuum diffusion process in a manner that produces bonds as strong as the parent metal.

As shown in FIG. 4B, which shows the sonic resonator assembly in more detail, the leading edge (from the signal input source) diameter of each disc within the lamina of discs which make up main resonator assembly 444 should have a "taper". Each disc progressing from the dual piezoelectric driver 442 up to the receiving piezoelectric device 450 should have a larger diameter (d) at the leading edge side of the disc, decreasing to a smaller diameter at the trailing edge side of the disc, which is closer to the receiving piezoelectric device 450. In addition, each disk has a thickness (t). This design requirement is shown in FIG. 4B. The total length of taper for main resonator assembly 444 is sum ($\Sigma$) of thicknesses $t_1$ through $t_7$. The total amount of taper for the main resonator is the largest diameter $d_1$ minus the smallest diameter $d_8$. The degree of taper is the length of taper divided by the amount of taper, so the degree of taper is equal to $\Sigma t_1$ through $t_7 \div (d_1 - d_8)$.

The taper is necessary to reduce the "edge" effects (radial vibration mode and effects of beam spread) and to support the need to have a smaller contact area (at the end of the coupling cone) which must be coupled to the biomaterial. These edge effects result in sonic losses along the radius of each of the discs that make up the resonator assembly. First, there is beam spread, in which some of the lateral sonic energy spreads from being a pure plane wave having an oblique bounce off the sides of the sonic device, producing sonic energy losses. In addition, the radial mode vibrations present from the piezoelectric and metallic discs can be destructive to the plane wave. To minimize these edge or loss effects, the diameter of each disc in the lamina of discs is changed to give the resonator assembly a taper. The taper in the main resonator assembly 444 shown in FIG. 4B is a linear taper. In the alternative the taper may be an exponential taper (not shown).

When the taper is linear, the percentage of taper (diminishing width divided by length of the element×100) of each disc is the same and the percentage of taper for the entire lamina of discs is the same. In the exemplary embodiment of the invention described herein, the percentage of taper was about 50%. It is contemplated that the percentage of linear taper of the main resonator assembly may vary from about 20% to about 70%.

FIG. 4B shows an expanded cross-sectional schematic of a "transparent" receiver assembly 450. The "transparent" receiver assembly 450 acts as an additional resonator disc during transmit calibration and transmitted power cycles, and as a receiver in pulse echo mode. It is "transparent" during transmission because it passes all signal energy coming from the other lamina discs, behaving as an additional resonator disc. To support this requirement to behave as an additional resonating disc, it must have the proper thickness and maintain a 1.3:1 to 3:1 impedance ratio. The transparent receiver assembly 450 (including all three elements), when present, is ratioed with respect to the disk immediately before the assembly, with the coupling cone disk 448 immediately following transparent receiver assembly 450.

As shown in FIG. 4B, the transparent receiver assembly 450 comprises the receiving piezoelectric element 446 sandwiched between two discs 452, where the two discs comprise the same material. The material comprising the two discs 452 is selected to match the acoustic impedance of the receiving piezoelectric element 446. Typical piezoelectric materials used in high power applications have an acoustic impedance in the range of about 36 MRayls (MKS). Brass comes in a variety of alloys which span the typical impedance value of the piezoelectric element. One of skill in the art to which the invention belongs will be able to select an appropriate alloy of brass to match the acoustic impedance of the piezoelectric element. The two discs which sandwich the piezoelectric element need to have the closest match to the piezoelectric element impedance which is reasonably possible. Therefore the Z of the discs will be near 36 MRayls.

The transparent receiver assembly 450 is constructed to have an effective thickness which provides a flight time of 1$\lambda$ (or an effective thickness which matches the effective thickness of other discs in the main resonator assembly). For example, if the nominal resonance frequency of the transmitting piezoelectric is 1 MHZ, the total receiver assembly would have a one-way flight time of 1 microsecond. If half of the flight time is allocated to the two brass discs and half to the piezoelectric element, the wavelength ($\lambda$) would be allocated to have each brass disc be 0.25$\lambda$ in effective thickness, and the piezoelectric element would be 0.5$\lambda$ in effective thickness.

The required effective thickness of the transparent receiver assembly is calculated using the velocity of sound in the receive piezoelectric disc times its allocated flight time plus the velocity of sound in the metal discs (brass alloy) times its allocation of flight time.

In the present exemplary embodiment, the brass discs 452A and 452B and the piezoelectric element 446 (collectively, the transparent receiver assembly 450) were of about (within ±10%) the same diameter, which matched the smallest diameter (shown as $d_x$ on FIG. 4B) of the last disc in the lamina of discs (which abuts the transparent receiver assembly 450). While the transparent receiver assembly may continue the taper of the main resonator, due to the brittleness of a typical piezoelectric element, it may be more practical to discontinue the taper after the conclusion of the main resonator assembly, so that the transparent receiver assembly has the same diameter as the end diameter $d_x$ of the main resonator assembly.

Referring back to FIG. 4B, the coupling element 448 is specifically designed to follow the alternating lamina scheme, that is, the coupling element 448 has an impedance ratio which ranges from 1.3:1 to 3:1 relative to the transparent receiver assembly 450. The material making up the coupling element should be a lower impedance metallic disc of the kind selected for the resonator stack (such as aluminum, for example and not by way of limitation). This provides an acoustic impedance gradient between the high Z discs in the main resonator assembly 444 and that of the biomaterial. The coupling cone may continue the taper of the main resonator assembly, which may be either linear or exponential.

As shown in FIG. 4B, the coupling element may be tapered to further reduce the resonator assembly's diameter to a smaller tip size. The desired tip size will be dependent on the biomaterial which is being treated. The largest diameter the coupling element 448 (which abuts the transparent receiver assembly 450 should be the same or about (i.e., within ±10%) the same as the diameter of the transparent receiver assembly 450. This diameter is the same as the smallest diameter ($d_x$) of the last disc in the lamina of discs, when the transparent receiving assembly is not tapered, as shown in FIG. 4B.

With further reference to FIG. 4B, examples of material layers making up the main resonator assembly 440 are as follows. The dual piezoelectric driver 442 comprises piezoelectric elements 441b and 443b, with a layer (disc) of low Z metal 441a in direct contact with the leading edge surface 439 of disc 441b. A second disc of low Z metal 443a is present between piezoelectric element discs 441b and 443b. The low Z metal layer is frequently aluminum. The main resonator assembly 444 includes 7 layers (discs), where the low Z discs (445A-445D) are formed from materials selected from the group consisting of aluminum, tin, titanium, indium, and combinations thereof, by way of example and not by way of limitation. The high Z discs (447A-447C) are formed from materials selected from the group consisting of copper, nickel, platinum, gold, molybdenum, and combinations thereof, by way of example and not by way of limitation. The transparent receiver assembly 450 includes a central layer (disc) 446 of a piezoelectric material, which is sandwiched between two layers (discs) 452A and 452B which are typically formed from a brass alloy which has a Z which is in the same range as the Z of the piezoelectric disc 446, an example would be brass 460. The coupling element 448 is also formed from a low Z material, such as aluminum, by way of example.

Calibration of the Ultrasonic Impulse Generator to Function in Combination with a Given Biomaterial For the sonic resonator system to function properly with a given biomaterial, it is necessary to calibrate the sonic resonator system the first time that the system is used with that particular biomaterial. Once a calibration has been developed and the proper wave forms have been generated by the computer/controller of the sonic resonator system for such biomaterial, it is not necessary to recalibrate the system, as long as the biomaterial properties remain constant.

With reference to FIG. 4A, the calibration method comprises the capture of a "calibration" sonic wave being emitted from the resonator assembly 440 by positioning a calibration sensor 490 at any selected location within the sonic near field of the resonator assembly. The captured calibration wave form produced is then digitized and passed along pathway 492, through pre-amplifier 460 and A/D converter 470 to the computer 410. Computer 410 makes use of a calibration algorithm described below to create a Power Pulse packet of waveforms which is used to achieve a "focus" of high sonic intensity at the location where the calibration sensor 490 was previously positioned. For the construction of both compression and rarefaction pulses at a desired location within a material being tested 480 (as shown in FIG. 4A), a calibration algorithm is used to construct the pulse at a location relative to the material being tested.

The transducer/resonator near field distance is about:

$$N.F.=d^2/k\lambda$$

Where d=diameter of the transmit piezoelectric element; $\lambda$=wavelength; and
k=a number about unity.

Calibration is performed using the following procedure:

1. Create a broadband signal (FIG. 6A, for example) to excite or stimulate the applied voltage signal I(t), of the sonic resonator assembly. For convenience, a desired final response impulse will be used for calibration; however, any signal having the bandwidth of the desired impulse may be used, which could be a positive-followed-by-negative impulse, or any phase.

When the resonator is calibrated, a signal is applied to stimulate or excite the resonator assembly. This signal (FIG. 6A, for example) is shown as a very wide bandwidth signal (an impulse) having only 1.5 cycles. For biomedical applications, other signal shapes may be used to simulate the resonator. The term "Excitation Waveform" is used herein to refer to the signal used to stimulate the resonator.

2. Apply the signal (as determined in Calibration Step 1, above) to the system and measure the Capture Waveform, C(t), as shown in FIG. 5A, which is a plot 500 of signal amplitude (in volts) on axis 502, as a function of time (in microseconds) on axis 504. Then, take the Fourier transform of this signal to obtain the amplitude and spectral response $A_C(f)$, as shown in FIG. 5B, which is a plot 510 of signal amplitude 512 as a function of signal frequency in MHZ (megahertz) on axis 514.

During calibration, the response of the system, the resonator assembly, and any biomedium in the acoustic path is captured by the acoustic sensing device. The term "Capture Waveform" is used herein to refer to the waveform collected by the acoustic capture device as a result of application of the Excitation Waveform.

3. Create a target response, T(f) (for example, the input impulse delayed in time), and take the Fourier transform, $A_T(f)$ and $\theta_T(f)$. This is an impulse at some specified time, T, after the start of the signal. If the target response is of the same shape as the impulse used for calibration, then the amplitude transforms are identical, and the phase functions are straight lines of different slopes. If corrections are made for dispersion or nonlinear propagation through the biomaterial, there may be a slight curve to the phase function.

FIG. 5C shows a bandwidth of a typical calibration response, and FIG. 5D shows a phase of the calibration response. FIG. 5C is a plot 520 showing signal amplitude on axis 522 as a function of signal frequency in MHZ on axis 524. FIG. 5D is a plot 530 of the phase angle of the capture waveform in radians on axis 532 as a function of signal frequency in MHZ on axis 534. The slope of the curve shown in FIG. 5D is not linear, but has a curve to it. The slope of the curve can be made more linear using the enhanced calibration method described in the embodiments below.

4. Take the inverse Fourier transform of the θs(f) to obtain the signal, s(t), which, when applied to the system produces an impulse at time T. A corresponding amplitude function, As(f), is needed to take the inverse transform needed to define the drive function that produces the impulse. Any amplitude function produces an impulse; however, the appropriate amplitude function depends on the application, as discussed below.

Before a discussion of the choice of amplitude function, consider three ways of defining performance:

1. Peak Power: One measure of the ratio of peak acoustic output power to average input electrical power. The practical question is, given a drive amplifier-transducer combination that can deliver a maximum electrical output drive power, what is the peak acoustic output power. This ratio is one measure of performance.

2. Figure of Merit: Another measure is the ratio of the peak acoustic output power to average acoustic output power. Configurations that produce high peak acoustic power at the specified time often have high leakage, i.e. relatively high acoustic output at times other than the specified time.

3. Bandwidth: The bandwidth of the acoustic impulse determines the width of the impulse. Monocycle impulses require large bandwidths. Transducers designed according to embodiments of the present invention can have bandwidths that exceed one decade and can produce impulses which are short in time period. There may be applications that require that the bandwidth be limited, to avoid beam spread that might occur at low frequencies. In such a case, the transducer can be driven with a signal having less bandwidth.

The following are four ways of choosing the amplitude function which will be best to produce the impulse needed for a test or treatment of a particular biomaterial:

A. Choose the amplitude transform of the calibration response function. This function produces a high amplitude impulse with corresponding high sonic leakage (some sonic energy spreads from being a pure plane wave having an oblique bounce off the sides of the sonic device, producing sonic energy losses) and a low figure of merit. This function has peaks of the amplitude transform at frequencies where there is good electrical impedance matching between the power amplifier and transducer and correspondingly efficient acoustic power generation by the transducer.

B. Choose the amplitude transform of the impulse used for calibration. This function produces a higher figure of merit than A., above, but a lower peak power, because energy is supplied to the transducer at frequencies where there is a poor electrical impedance matching between the amplifier and the transducer.

C. Choose $1/(A_C(f)+\epsilon)$, where $\epsilon$ is a small number, to prevent this function from becoming infinite. This produces the highest figure of merit with the lowest peak power. In this case, high electrical amplitudes are applied to equalize the output spectrum at frequencies where the transducer has low electrical-to-acoustic efficiency.

D. Choose any of the amplitude functions, but put the function through a window (such as a Hamming window) to limit the electrical bandwidth (hence acoustic bandwidth). The effect of this is to remove any unwanted acoustic frequencies from the output at the expense of making the impulse longer, i.e., the impulse will have multiple cycles.

The Capture Waveform is processed according to the disclosed calibration software algorithm to produce a new signal—referred to herein as the "Power Packet"—that is, a complex waveform applied to the resonator assembly to produce the high intensity, wide bandwidth, sonic pulse concentrated (focused) at the location where the calibration acoustic sensor was located.

Enhanced Calibration Method to Correct for Phase Errors

The above descriptions are related to methods of providing the best apparatus to be used and the method to be applied to provide an ultrasonic impulse to a biomaterial for therapeutic, cosmetic or aesthetic, diagnostic, exploratory, non-invasive, or other medical procedures. It is also important to address a correction for phase errors which are due to nonlinear or dispersive propagation of a calibration signal into the biomaterial.

Whether the biomaterial is nonlinear or dispersive, the sonic propagation characteristics of the media depend on the amplitude of the sonic signal, both as a function of time and the position in the three dimensional biomaterial. The propagation of the calibration signal is different than the impulse signal, because of the amplitude differences. The higher amplitude signal produces harmonic frequencies not present in the signal emitted by the resonator, and these signals add to the transmitted wave, to distort the signal. In addition, there is an apparent increase in attenuation of the transmitted signal to supply the energy for the harmonic signals that are generated.

It is an objective of embodiments of this invention to produce high intensity sonic impulses of the desired shape after the wave travels through the media. If the resonator was calibrated as in the first embodiment, the impulse would change shape as it propagated through either a dispersive or nonlinear media. The calibration procedure must be extended by the following means:

After a first calibration procedure is complete, the full amplitude resultant response captured by the sensing transducer is processed to get the phase error (shown in FIG. 5E). The phase amplitude error is subtracted from a linear straight line phase response to produce a phase correction factor (shown in FIGS. 5F and 5G). This phase error correction factor is then added to the phase of the original drive signal to produce a corrected drive signal. This new drive signal is then applied at full amplitude. This process is repeated until the phase of the detected signal is sufficiently linear.

FIG. 5H shows a waveform (Power Packet) which is the result of a calibration procedure where considerations B ("Choose the amplitude transform of the impulse used for calibration.") and D("Choose any of the amplitude functions, but put the function through a window") described above were utilized. Referring to FIG. 4A, this Power Packet is then passed from computer/controller 410 through the D/A converter 420 through a signal splitter 422 (when there are dual driving transducers in the resonator assembly 440), through preamps 430 and 432, and is applied to piezoelectric elements 441b and 443b, which are present the dual piezoelectric driver 442, which is present in the sonic resonator assembly 440 shown in FIG. 4A. The transfer of sonic waves from the dual piezoelectric driver 442 into the main resonator 444 through the receiver assembly 450 and through coupling cone 448 will produce a high power, wide bandwidth impulse concentrated (focused) as a power pulse at a location within a biomaterial (not shown) where the acoustic capture device 490 was located during the calibration process. This location is illustrated at the interface between biomaterial 480 and capture device 490, as illustrated in FIG. 4A.

FIGS. 6A and 6B, respectively, show an example of an applied Excitation Waveform, I(t), and amplitude, $A_f$, transform for the applied signal. FIG. 6A is a plot 600 showing signal amplitude (in volts) on axis 602 as a function of time (in microseconds) on axis 604. The waveform (signal) shown in FIG. 6A is just one example of a waveform that can be used to excite the resonator: however, in some embodiments of biomaterial testing or treatment, an optimal impulse would be as shown in FIG. 6A.

FIG. 6B is a plot 610 showing signal amplitude (in volts) on axis 612 as a function of signal frequency in MHZ (Hz×10$^6$) on axis 614. A Fourier transform of this impulse (or other signal) provides an amplitude, $A_f(f)$ which can be used in the algorithms previously disclosed herein.

An Exemplary Sonic Resonator System for Use in Biomedical Applications

The objective of the calibration procedure is to produce a high concentration of sonic energy of a desired shape and amplitude after the wave travels into the sample of biomaterial 480 (as illustrated in FIG. 4A) to the desired depth. After the calibration process using the overall system 400 shown in FIG. 4A, which includes the resonator assembly 440, coupling device 448, biomaterial 480 and acoustic capture device 492, it is then possible to achieve a concentration or "focus" of a high sonic intensity compression or rarefaction pulse at a specific near field location within the same type of biomaterial using the sonic resonator system 700 shown in FIG. 7A, which is absent the acoustic capture device 492 of system 400.

The sonic resonator system 700 shown in FIG. 7A includes a controller 710, typically a computer, which is used to generate a waveform that is passed through a digital-to-analog (D/A) converter 720 and into an input splitter 722, which sends a signal to a plurality (two are shown in FIG. 7A) of power amplifiers (730 and 732), which are in communication with a dual piezoelectric assembly 742 which comprises a plurality of transducers 741 and 743 (which are described in more detail below with respect to FIG. 7B), which provide input to a resonator assembly 740. The piezoelectric elements (741b and 743b in FIG. 7B) convert electrical energy into acoustic energy. The acoustic energy is input into the main resonator laminate 744 which stores the energy and passes the energy into a biomaterial 780 through a coupling device 748. The waveform which is fed into the transducers provides a wideband acoustic impulse having a much higher peak power than the peak power that can be produced by the transducers alone. Multiple high peak power wideband acoustic impulses can be placed within the near field beam of the biomaterial 780 as desired. The resonator assembly apparatus 740 typically includes a receiver 750 which comprises three layers (as illustrated in detail in FIG. 7B), where layers (discs) 752A and 752B are of a metal material which corresponds with a piezoelectric element 746 as previously described. The receiver is used to capture backscatter from the biomaterial 780. During clinical procedures, the piezoelectric receiver 750 is connected to the computer 710 through a pre-amplifier 760 and A/D converter 770, as illustrated by pathway 754 in FIG. 7A.

Referring to FIG. 7B, which is an expanded cross-sectional side-view of the sonic resonator assembly 740 shown in FIG. 7A, a high intensity power pulse is produced at a location 706, present within biomaterial 780 along axis 705. Locating the acoustic capture device 490 as shown in FIG. 4 at positions along axis 705 during the calibration of the resonator assembly 440 illustrated in FIGS. 4A and 4B will produce oval-shaped focal zones 706, as illustrated in FIG. 7C. The sonic energy enters the near field location 704 from surface 703, which is the contact surface between the coupling device 748 and biomaterial 780, and travels along axis 705. Locating the acoustic capture device at a position which is off axis from axis 705, at a new axis 707, for example, as illustrated in FIG. 7D, will produce an annular ring of sound intensity within biomaterial 780 which has a radius equal to the lateral position from the axis of the resonator assembly 740, due to the cylindrical symmetry of the resonator assembly 740. The on-axis zone of high intensity is shown as annular ring 708, while the lateral-position-adjusted annular rings 709a and 709b show the change in position along new off-axis 707, and the change in size of the area in which the annular ring is present. Increased lateral position from the axis of the resonator assembly 740 increases the size of the annular ring of high sonic energy, but reduces the intensity of the energy present within the annular ring. Particular biomedical treatments would benefit from use of a larger area of lower intensity sonic energy, which can be accomplished using off axis angle calibrations. Off axis annular rings of acoustic intensity may be augmented by use of multiple resonator assemblies that overlap their annular rings of sonic intensities.

Multiple Resonator Assemblies

As mentioned above, in some applications, it may be beneficial to use multiple resonator assemblies 740 of the kind shown in FIGS. 7A and 7B. Multiple resonator assemblies may be arranged to produce overlapping sonic fields as shown in FIG. 8A, where axes 802, 804, and 806 represent the axes of sonic fields produced by a combination of three resonator assemblies (not shown). This permits additional modes of operation, i.e., simultaneous and interleaving of selected focus areas. In simultaneous mode, the focus from each resonator assembly is positioned to be at the same time within the waveform (at the same location within the overlapping sonic fields, with each synchronized to produce an acoustic intensity greater than an individual resonator assembly). In an interleaved mode, the focus areas from each resonator assembly would be advanced to different locations, to get greater area coverage in a shorter period of time. To reduce the size of the surface area needed to couple into the biomaterial under study, each resonator assembly is positioned to take advantage of its tapered sides, to properly aim the axis of each resonator assembly at the desired, specific position. If the sides of the resonator assembly are linearly tapered, as shown in FIGS. 7A and 7B, for example, then the axis of each resonator assembly can be fixed in position by the use of a sonically isolating material. In an alternative embodiment, a mechanical positioning system may be utilized to provide variable positioning of each sonic resonator assembly's axis at a location advantageous for a particular treatment. If the sides of the resonator assembly are curved (exponential taper), not shown in the present drawings, a more complex assembly can be realized, using a molded housing to properly join the resonator assemblies.

FIGS. 8B and 8C show a dual piezoelectric drive, dual resonator assembly design for use in the sonic resonator system. However, other arrangements of more than two resonator assemblies may be used as well. FIG. 8B shows a housing 810 designed to enclose a dual resonator assembly, where a first resonator assembly is enclosed is section 812A and a second resonator is enclosed in section 812B of the housing 810. The area 814 of the housing 810 is used in contact with the biomaterial (not shown). FIG. 8C shows the dual resonator assembly 820, which includes assemblies 822A and 822B which are present in housing 810. Resonator assembly 822A includes the dual piezoelectric driver 842A, the main resonator assembly 844A, the transparent receiver assembly 850A, and the coupling device 848A, which makes contact with biomaterial 880 at surface 824A. Resonator assembly 822B includes the dual piezoelectric driver 842B, the main resonator assembly 844B, the transparent receiver assembly 850B, and the coupling device 848B, which makes contact with biomaterial 880 at surface 824B. Area 860 illustrates a sonically isolating material used to join the two resonators.

FIGS. 8A and 8B show the arrangement of two sonic resonator assemblies, but arrangements of more than two can be easily implemented to further expand the number of overlapping sonic fields. A combination of any number of resonators, depending on size, can be constructed using a more complex assembly to align the axis of each sonic resonator assembly while having a contact area with the biomaterial which is of a specified size.

The waveform created by the resonator assembly at the "focus", within the biomaterial (not shown) which is being treated is referred to as the "Power Pulse".

FIGS. 9A and 9B are examples of actual Power Pulses created by the sonic resonator of the invention after application of a Power Packet. FIG. 9A is a plot 900 showing signal amplitude (in volts) on axis 902 as a function of time (in microseconds) on axis 904 when the focused impulse 903 created is a compression pulse; FIG. 9B is a plot 910 showing signal amplitude (in volts) on axis 912 as a function of time (in microseconds) on axis 914 when the focused impulse 913 created is a rarefaction pulse. The goal for the sonic energy outputs illustrated in FIGS. 9A and 9B was that the sonic energy was in the form of short, powerful impulses, 903 and 913 as illustrated.

FIG. 9C, which is a plot 920 showing signal amplitude (×10$^5$) on axis 922 as a function of frequency (in MHZ) on axis 924, shows the bandwidth of the rarefaction Power Pulse 903 illustrated in FIG. 9A.

Not all applications of embodiments of the present invention call for a short, powerful impulse to be delivered at one location within the biomaterial being tested or treated. As discussed previously, there are apparatus modifications which enable applying the sonic energy over a larger area within a biomaterial which is being treated. The time period for treatment may need to be a long period rather than a short period. The question then becomes which form the Power Packet waveform applied to the driving transducers should take. For this reason and other reasons, it is important to calibrate the sonic resonator system to work with the biomaterial which is being tested or treated.

Reducing Power Loss Across the Main Resonator Assembly

One method of reducing power loss or leakage within a sonic resonator assembly is to reduce the amount of power which is lost due to radial surface waves which are generated on the discs which are laminated to form the main resonator assembly 744 shown in FIG. 7A, for example.

In one embodiment of the invention, the discs which make up the main resonator assembly 744 may be altered in a manner which increases the efficiency of the transfer of the acoustic wave through the assembly 740.

FIG. 10A shows a surface view and FIG. 10B shows the matching cross-sectional view of a resonator disc 1002 which has a radial kerf 1008 cut into a surface 1003 of disc 1002. The purpose of the radial kerf is to align in time the radial surface wave with the plane wave reverberation in a given disk, to improve the efficiency of the resonator assembly. A number of kerfs may be used on a disc surface, depending on the diameter of the disc.

Since the main resonator assembly comprises lamina of metallic discs, when the plane (longitudinal) wave generated by the piezoelectric element strikes the discontinuity between any two of these discs having different acoustic characteristics, various additional waves are generated. The major sound wave generated as a result of the primary plane wave striking the interface between two discs is a radial surface wave which is sometimes referred to as a plate wave. This radial surface wave starts from the impedance discontinuity at the outer radius of each metallic disc when the generated plane wave passes the interface between lamina (discs). With reference to FIG. 10C, which shows a cross-sectional view 1020 of disc lamina L1, L2, and L3, the radial surface wave velocity created at laminal interfaces 1033 and 1035 is dependent in a very complicated way on the material, its thickness, the material to which it is joined and the ultrasonic frequency. This velocity is more easily obtained by laboratory measurement rather than trying to calculate it. The measured velocity of this radial surface wave is in the range of 2000 msec and is about one third of the plane wave velocity in a typical disc. FIG. 10C shows the generation of radial surface waves 1024 and 1028, which occur at the interfacial surfaces 1033 and 1035 between the disc laminae L1, L2, and L3. With reference to the disc 1002 top view illustrated in FIG. 10A, the radial surface wave will reach a peak at the center of the disk 1002, and will repeat each odd multiple of the Flight Time from the edge to the center, where Radial Flight Time(t) is calculated as follows:

$$RFT(t) = \text{Radial Distance }(Rd)/\text{Velocity }(V)\text{ of the surface wave}$$

This RFT(t) is then the time for the radial surface wave to travel from the outer circumference of the disc to the center and then repeats when traveling through the center to the outer edge and then back to the center again, resulting in the odd multiple of Flight Time, i.e., 1, 3, 5, etc.

In one embodiment of the invention, the RFT is matched to the two-way PFT of the plane wave 1022, illustrated in FIG. 10C for a given disc. Where the PFT of the plane wave in the given disc is:

$$PFT(t) = \text{Disk Thickness}(X_d)/\text{Velocity }(V)\text{ of the plane wave}$$

Because the radius of the disk in a resonator assembly may not allow for the desired alignment (in time) of the radial surface wave with the plane wave in a given disc, a radial kerf is cut into the disc to establish the proper FT alignment of the radial surface wave with the FT of the plane wave. The kerf creates a new "edge" for the radial surface wave to form and start from.

The radius at which the kerf is cut into the disc is determined by:

$$R_{kerf} = 2 * FT_{plane\ wave} * V_{radial\ wave}/N$$

where N is odd integer values 1, 3, 5, etc.

The result of cutting a kerf in a metallic disk equal to $R_{kerf}$ is to align (in time) the radial surface wave with the plane wave reverberation in that disk, so that both waves reach an acoustic peak at the same time. Addition of a kerf improves the efficiency of the resonator by "capturing" the acoustic radial surface wave energy that would normally be a lossy or destructive wave if it were not forced to properly align with the plane wave.

FIG. 10B shows a cross-sectional view of FIG. 10A, illustrating the radial kerf 1008 and the depth and width of the kerf. Cutting of a kerf of the kind shown in FIG. 10A into the front face of the disc aligns (in time) the radial surface wave with the plane wave reverberation in that disc, so that both waves reach an acoustic peak at the same time. The kerf is typically cut into the surface of the disk facing in the direction of propagation of the plane wave. Kerfs may be cut in all of the discs, but are typically cut into selected discs. As the amplitude of the plane wave diminishes, after passing through the resonator stack, there is less advantage to having a kerf.

FIG. 10A shows the position of a kerf 1008 in a typical disc 1002 which may be present in a main resonator assembly 744 of the kind shown in FIGS. 7A and 7B. The radius "R1" (1010) shown in FIG. 10A is the $R_{kerf}$ that was calculated from the equation provided above. The width of the kerf, illustrated as "w" (1005) on cross-sectional view of disc 1002, which is provided in FIG. 10B, should be less than 0.030 inch and have a minimum depth of 0.030 inch with a maximum depth "d" (1007) of half of the thickness of the disc.

"R2" (1012) illustrated in FIG. 10A shows the location of a second radial surface wave peak that results from cutting a kerf at R1. This new radial wave peak occurs at half the difference in distance between the kerf at R1 and the outer radius "R3" (1014) illustrated in FIG. 10A. Given the largest disc radius and the taper of a typical main resonator assembly, the acoustic peak of the second radial surface wave at R2 may also not align with the acoustic peak of plane wave per the $R_{kerf}$ equation, so that both waves reach an acoustic peak at the same time.

The addition of a second kerf (not shown) would produce a third radial surface wave peak at half the distance between the second kerf and the outer edge of the disk. A third kerf could be cut to again align this new radial surface in time with the plane wave. A practical limit will quickly be reached for additional kerfs beyond two kerfs in a single disc unless the discs are greater than 2 inches in diameter.

Clinical Procedure

A typical clinical procedure using the sonic resonator system described herein provides much more control over the positioning of the concentrated sonic energy in the biological medium and control of the amount of sonic energy applied than conventional devices. For clinical applications where the anatomical structures are near (i.e., fatty tissue) the skin surface, hand manipulation is possible. For clinical applications involving deeper structures and for very specific areas of sonic concentration, a mechanical positioning system linked to a separate imaging system can be used to position the resonator to precisely target these anatomical areas.

Substituting the acoustic sensing device (FIG. 3A, 390) with a needle or catheter hydrophone placed at the location where the "focus" should occur, permits in-vivo calibration. Polymer piezoelectric material such as poly vinylidene fluoride (PVDF) will make a very small acoustic sensing device that can be added to a small diameter needle or part of a catheter for insertion into the bio-medium. The calibration of the resonator system (Capture Waveform) is then completed using this needle or catheter hydrophone to insure exact concentration of acoustic intensity (focus) within the bio-medium. The needle or catheter transducer can also be used as a "beacon" to monitor the sonic intensity and resulting tissue change.

Improved backscatter sensitivity and receive focus capability can be added to the resonator with a thin film annular array attached to the coupling element (FIG. 4A, 480). The thin film 3 to 5 annuli array made using a polymer piezoelectric material (PVDF) would augment or substitute for the transparent receiver (FIG. 4A, 450) and be attached to the front surface of the coupling element.

Because the sonic resonator can concentrate ("focus") the energy at any location within it's sonic near field electronically, and with its included receive capability, real-time feedback is given to the operator to adjust the sonic intensity and "focal" location to precisely treat a much greater area, without being physically repositioned like a fixed focus device. The sonic resonator also delivers a lower level sonic field across its total surface area in contact with the skin, and can then concentrate sonic energy to selected locations, so only the very small area selected by the user is subjected to high levels of sonic energy. Calibration would be conducted using representative tissue samples in the laboratory and saved in the computer as look up tables for later selection by the clinician.

The above described exemplary embodiments are not intended to limit the scope of the present invention, as one skilled in the art can, in view of the present disclosure, expand such embodiments to correspond with the subject matter of the invention claimed below.

We claim:

1. A sonic resonator system which is used to apply a power pulse at at least one selected location within a biomaterial, wherein said system comprises:
   a computer containing software algorithms for signal reconstruction and at least one wave form generator;
   at least one D/A converter, which communicates with said computer and which sends a signal to at least one power amplifier;
   said at least one power amplifier, which sends a signal to at least one piezoelectric transducer element which is in communication with a sonic resonator assembly;
   at least one sonic resonator assembly in communication with said wave form generator, where said at least one main resonator assembly transmits sonic energy into said biomaterial, where said sonic energy includes at least one power pulse within at least one wave generated using input from said at least one wave form generator, and wherein said at least one sonic resonator assembly is in communication with a coupling element, and wherein at least one coupling agent may be in contact with said biomaterial;
   a removable calibration sensor, which, when present, provides input to said computer; and
   an A/D converter, which provides a signal to said computer from said removable calibration sensor, when present, or from said coupling agent through said biomaterial when said calibration sensor is not present.

2. A sonic resonator system in accordance with claim 1, wherein said computer algorithms enable putting an amplitude function through a window to limit acoustic bandwidth.

3. A sonic resonator system in accordance with claim 1, wherein said sonic resonator assembly includes discs where a surface of at least one disk has been altered by forming at least one kerf in said disc, so that an efficiency of said resonator assembly is improved.

4. A sonic resonator system in accordance with claim 3, wherein said kerf is a radial kerf.

5. A sonic resonator assembly in accordance with claim 1, wherein at least a portion of discs present in a main resonator assembly which is part of said sonic resonator assembly are of a construction which alternates between high Z acoustic material and low Z acoustic material.

6. A sonic resonator assembly in accordance with claim 5, wherein an impedance ratio between a disc containing a wave before an interface and a disc containing a wave after an interface ranges from about 1.3:1 and about 3:1.

7. A sonic resonator assembly in accordance with claim 6, wherein a high Z material is selected from the group consisting of nickel, platinum, gold, molybdenum, and combinations thereof, and a low Z acoustic material is selected from the group consisting of aluminum, tin, titanium, indium, and combinations thereof.

8. A sonic resonator system which is used to apply a power pulse at at least one selected location within a biomaterial, wherein said system comprises:
 a computer containing software algorithms for signal reconstruction and at least one wave form generator;
 at least one D/A converter, which communicates with said computer and which sends a signal to at least one power amplifier;
 said at least one power amplifier, which sends a signal to at least one piezoelectric transducer element which is in communication with a sonic resonator assembly;
 at least one sonic resonator assembly in communication with said wave form generator, where said at least one sonic resonator assembly transmits sonic energy into said biomaterial, where said sonic energy includes at least one power pulse within at least one wave generated using input from said at least one wave form generator, and wherein said at least one sonic resonator assembly is in communication with a coupling element, and wherein at least one coupling agent may be in contact with said biomaterial;
 at least one removable calibration sensor, which, while present, provides input to said computer, so that said sonic resonator system may be calibrated to provide a desired outcome in a particular biomaterial, and wherein said at least one calibration sensor is located in series after said at least one sonic resonator assembly and after a location at which a sample of biomaterial is placed between said at least one sonic resonator assembly and said at least one calibration sensor; and
 an A/D converter, which provides a signal to said computer from said removable calibration sensor, when present, or from said coupling agent through said biomaterial when said calibration sensor is not present.

9. A sonic resonator system in accordance with claim 8, wherein said removable calibration sensor is removed during application of a power pulse to a biomaterial to be treated.

10. A sonic resonator system in accordance with claim 8, wherein said system includes a pre-amplifier and an analog to digital converter between each calibration sensor and said computer.

11. A sonic resonator system in accordance with claim 8 or claim 9, or claim 10, wherein said calibration sensor is an acoustic capture device.

12. A sonic resonator system in accordance with claim 1, wherein said sonic resonator system also comprises at least one signal splitter between said computer and said at least one resonator assembly.

13. A sonic resonator system in accordance with claim 1 or claim 12, or claim 8, wherein said at least one power pulse within said at least one wave generated using input from said at least one wave form generator is aligned to travel along at least one axis selected from the group consisting of a single axis, a plurality of axes, and a path which is off axis from a centerline of a target biomaterial which is being treated using said at least one power pulse.

14. A sonic resonator system in accordance with claim 1 or claim 12, or claim 8, wherein a transducer present within a sonic resonator assembly may be driven with a signal which has a bandwidth which exceeds one decade, so that a short power pulse is produced.

15. A sonic resonator system in accordance with claim 1, or claim 12, or claim 8, wherein said sonic resonator assembly includes a driving transducer which may be driven with a signal having a bandwidth lower than one decade.

* * * * *